US009151767B2

(12) United States Patent
Yang

(10) Patent No.: US 9,151,767 B2
(45) Date of Patent: *Oct. 6, 2015

(54) ANALYTE SENSORS

(75) Inventor: Jenny J. Yang, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 161 days.

This patent is subject to a terminal disclaimer.

(21) Appl. No.: 10/914,769

(22) Filed: Aug. 9, 2004

(65) Prior Publication Data

US 2006/0030029 A1  Feb. 9, 2006

(51) Int. Cl.
*G01N 31/00* (2006.01)
*G01N 33/53* (2006.01)
*G01N 33/84* (2006.01)
*G01N 33/542* (2006.01)

(52) U.S. Cl.
CPC .............. *G01N 33/84* (2013.01); *G01N 33/542* (2013.01)

(58) Field of Classification Search
CPC ..... G01N 21/05; G01N 21/78; G01N 21/643; G01N 21/645; G01N 21/6428; G01N 21/8483; G01N 31/22; G01N 33/84; Y10S 435/00; Y10S 436/00; Y10S 436/807
USPC ............ 422/82.05, 82.08; 436/74, 78, 81, 87, 436/82, 172

See application file for complete search history.

(56) References Cited

U.S. PATENT DOCUMENTS

| 5,679,548 | A | 10/1997 | Barbas et al. | 435/69.6 |
| 6,197,258 | B1* | 3/2001 | Thompson et al. | 422/82.07 |
| 6,469,154 | B1 | 10/2002 | Tsien et al. | |
| 2002/0160473 | A1* | 10/2002 | Lukyanov et al. | 435/183 |
| 2003/0149254 | A1* | 8/2003 | Anderson et al. | 536/23.1 |
| 2006/0029942 | A1 | 2/2006 | Yang et al. | |
| 2006/0031020 | A1 | 2/2006 | Yang et al. | |

FOREIGN PATENT DOCUMENTS

EP         1238982 A      9/2002

OTHER PUBLICATIONS

Kawasaki et al., "Classification and evolution of EF-hand proteins", BioMetals, 1998, vol. 11, pp. 277-295.*
Miyawaki et al., "Fluorescent indicators for Ca2+ based on green fluorescent proteins and calmodulin", Nature, 1997, vol. 388, pp. 882-887.*
Prasher et al., "Primary structure of the *Aequorea victoria* green-fluorescent protein", Gene, 1992, vol. 111, pp. 229-233.*
Wilkins et al., "Metal-binding studies for a de novo designed calcium-binding protein", Protein Engineering, 2002, vol. 15, pp. 571-574.*

Yang, J. et al., "Obtaining site-specific calcium-binding affinities of calmodulin", Protein and Peptide Letters, 2003, vol. 10, pp. 331-345.*
Yang, W. et al., "Rational design of a calcium-binding protein", J. Am. Chem. Soc., 2003, vol. 125 pp. 6165-6171.*
Ye et al., "Metal binding affinity and structural properties of an isolated EF-loop in a scaffold protein", Protein Engineering, 2001, vol. 14, pp. 1001-1013.*
Response to Non-Final Office Action filed Jul. 24, 2009 for U.S. Appl. No. 10/914,573.
Response to Non-Final Office Action filed Jul. 24, 2009 for U.S. Appl. No. 10/914,572.
Yang et al., Rational Design of a Calcium-Binding Protein. Journal of the American Chemical Society. Apr. 2003. vol. 125, pp. 6165-6171.
Mesecar, et al.; Orbital Steering in the Catalytic Power of Enzymes: Small Structural Changes with Large Catalytic Consequences. Science. Jul. 11, 1997; 277 (5323): 202-6.
Entry for Quatenary Structure. Oxford Dictionary of Biochemistry and Molecular Biology. Oxford University Press, Smith et al. (Ed) New York, 1997, p. 551.
Ye, e tal.; A Grafting Approach to Obtain Site-Specific Metal-Binding Properties of EF-Hand Proteins; Protein Engineering, vol. 16, No. 6; pp. 429-434, 2003.
Ye, et al.; Metal Binding Affinity and Structural Properties of an Isolated EF-Loop in a Scaffold Protein; Protein Engineering; vol. 14, No. 12; pp. 1001-1013; 2001.
MacKenzie, et al.; Bifunctional Fusion Proteins Consisting of a Single-Chain Antibody and an Engineered Lanthanide-Binding Protein; Immunotechnology 1 (1995) pp. 139-150.
Lee, et al.; Isolated EF-Loop III of Calmodulin in a Scaffold Protein Remains Unpaired in Solution Using Pulsed-Field-Gradient NMR Spectroscopy; Biochimica et Biophysica Acta; 1598 (2002); pp. 80-87.
Miyawaki, et al.; Flourescent Indicators for $Ca^{2+}$ Based on Green Fluorescent Proteins and Calmodulin; Nature; vol. 388; Aug. 28, 1997; pp. 882-887.
Prasher, et al.; Primary Structure of the *Aequorea victoria* Green-Fluorescent Protein; Gene; 1992; vol. 111, pp. 229-233.

(Continued)

*Primary Examiner* — Lisa Cook
(74) *Attorney, Agent, or Firm* — Thomas Horstemeyer, LLP

(57) ABSTRACT

Described herein are analyte sensors with a tailored analyte binding motif that binds an analyte and a host protein operatively linked to the analyte binding motif, in which the binding of the analyte to the analyte binding motif produces a detectable change and manipulation of the analyte binding motif manipulates the responsiveness of the sensor. Also described herein are methods for constructing an analyte sensor by constructing a tailored analyte binding motif capable of responding to an analyte and operatively inserting the analyte binding motif into a host protein. Included is a method for quantifying an analyte by introducing a nucleotide sequence for a protein having an analyte sensor with a tailored analyte binding motif that is able to produce a detectable change upon excitation, expressing the protein, providing excitement to the analyte sensor, and quantifying the detectable change. Nucleic acid sequences for an analyte sensor with a tailored analyte binding motif sequence for an analyte binding peptide that produces a detectable change upon excitation and a host sequence for a host protein, in which the tailored binding motif sequence and the host protein sequence are operatively linked, and manipulation of the analyte binding motif sequence manipulates the responsiveness of the analyte sensor are also included.

33 Claims, 12 Drawing Sheets

(56) References Cited

OTHER PUBLICATIONS

Yang, et al.; Obtaining Site-Specific Calcium-Binding Affinities of Calmodulin; Protein and Peptide Letters; vol. 10, No. 4; pp. 331-345; 2003.
Wilkins, et al.; Metal-Binding Studies for a de novo Designed Calcium-Binding Protein; Protein Engineering; vol. 15, No. 7; 2002; pp. 571-574.
Kawasaki, et al.; Classification and Evolution of EF-Hand Proteins; BioMetals; 1998, vol. 11; pp. 277-295.
Todd, Richmond, et al., "Engineered Metal Binding Sites on Green Fluorescence Protein" Biochemical and Biophysical Research Communications, vol. 268, No. 2, Feb. 16, 2000, pp. 462-465.
Romoser, Valerie, et al., "Detection in Living Cells of Ca-2+-dependent Changes in the Fluorescence Emission of an Indicator Composed of Two Green Fluorescent Protein Variants Linked by a Calmodulin-binding Sequence: A New class of Fluorescent Indicators," Journal of Biological Chemistry, vol. 272, No. 20, 1997, pp. 13270-13274.
Nagai, et al., "Circularly Permuted Green Fluorescent Proteins Engineered to Sense Ca2+" Proceedings of the National Academy of Sciences of USA, National Academy of Science, Washington, DC, vol. 98, No. 6, Mar. 13, 2001, pp. 3197-3202.
Wilkins, Anna L., et al. "Metal-Binding Studies for a De Novo Designed Calcium-Binding Protein", Protein Engineering, vol. 15, No. 7, Jul. 2002, pp. 571-574.
Hellinga HW et al., "Protein Engineering and the Development of Generic Biosensors," Trends in Biotechnology, vol. 16, No. 4, 1998, p. 183-189.
Supplementary European Search Report dated Aug. 25, 2009, for EP 05 78 3374.
Elbanowski, et al. Fluorescence of Lanthanide (III) Complexes in Aqueous Solutions: The influence of pH and solution composition. Monatshfte fur Chemie, 1985, vol. 116, pp. 901-911.
Johnson, et al., Structural Changes Required for Activation of Protein C are induced by CA2+ Binding to a High Affinity Site that Does Not Contain g-Carboxyglutamic Acid. The Journal of Biological Chemistry, 1983, vol. 258, pp. 5554-5560.
Lewis, et al. Fluorescence Binding Assay for an Small Peptide Based on a GFP fusion Protein. Analytica Chimica Acta., vol. 397, 1999, pp. 279-286.
Schlyer, et al. Time-resolved room temperature protein phosphorescence: Nonexponential decay from single emitting tryptophans. Biophysical Journal, vol. 67, 1994, pp. 1192-1202.
Yang; U.S. Appl. No. 10/914,769, filed Aug. 9, 2004.
Yang; U.S. Appl. No. 10/914,572, filed Feb. 9, 2006.
Shelling et al. Protein Nuclear Magnetic Resonance Studies of the Interaction of the Lanthanide Yetterbium and Lutetium with Apo- and Calcium Saturated Porcine Intestinal Calcium Binding Protein. Biochemistry, 1985, vol. 24, pp. 2332-2338.
Yang et al. The Molecular Structure of Green Fluorescent Protein. Nature Biotechnology, vol. 14, 1996, pp. 1246-1251.
Yang; Non-Final Office Action mailed May 17, 2007 for U.S. Appl. No. 10/914,572, filed Aug. 9, 2004.
Yang; Final Office Action mailed Feb. 26, 2008 for U.S. Appl. No. 10/914,572, filed Aug. 9, 2004.
Yang; Non-Final Office Action mailed Sep. 30, 2008 for U.S. Appl. No. 10/914,572, filed Aug. 9, 2004.
Yang; Non-Final Office Action mailed Mar. 31, 2009 for U.S. Appl. No. 10/914,572, filed Aug. 9, 2004.
Yang; Final Office Action mailed Nov. 25, 2009 for U.S. Appl. No. 10/914,572, filed Aug. 9, 2004.
Yang; Non-Final Office Action mailed Aug. 2, 2006 for U.S. Appl. No. 10/914,573, filed Nov. 9, 2004.
Yang; Non-Final Office Action mailed Nov. 16, 2007 for U.S. Appl. No. 10/914,573, filed Nov. 9, 2004.
Yang; Non-Final Office Action mailed Feb. 25, 2009 for U.S. Appl. No. 10/914,573, filed Nov. 9, 2004.
Yang; Final Office Action mailed Mar. 23, 2010 for U.S. Appl. No. 10/914,573, filed Nov. 9, 2004.

\* cited by examiner

Monitoring Metal-Binding Affinity of Grafted EF-loop

Tb$^{3+}$ Sensitized Energy Transfer

Excitation = 283 nm

Emission = 545 nm

- —— 2 μM CaM-CD2-III-5G-52
- --- 3 μM Tb
- —— 11 μM Tb
- --- 29.1 μM Tb
- —— 74.1 μM Tb

Electrospray Ionization Mass Spectrometry

ANALYTE SENSORS

SEQUENCE LISTING

This application contains a sequence listing filed in electronic form as an ASCII.txt file entitled 2207021030 ST25.txt, created on Oct. 25, 2010, and having a size of 8800 bytes. The content of the sequence listing is incorporated herein in its entirety.

BACKGROUND OF THE INVENTION

1. Technical Field

This invention generally relates to analyte sensors and methods for detecting or quantifying analytes. More particularly, this invention relates to fluorescent protein sensors for detecting and quantifying analytes, including $Ca^{2+}$ and $Tb^{3+}$, or for detecting proteins under in vivo and in vitro conditions.

2. Prior Art

Analytes, including $Ca^{2+}$, are essential to life and control numerous cellular processes such as cell division and growth, secretion, ion transport, muscle contraction, and neuron signaling through interaction with proteins. Further, analytes such as calcium, magnesium, iron and other metal ions are essential to biological systems through interaction with nucleic acid, lipids, carbohydrates and biometabolic molecules. Not only are many analytes essential structural components, e.g. $Ca^{2+}$ in teeth and bones, but analytes also act as second messengers regulating many biological processes during the birth, life, and death of cells. Furthermore, analyte-mobilizing agents such as ATP, histamine, glutamine, and second messengers such as inositol triphosphate (IP3) and CADPR affect the cytosolic concentration of $Ca^{2+}$ with defined spatio-temporal patterns.

As temporal and spatial changes in analyte concentration have significant consequences in biological processes, detection and quantification of the local analyte concentration in vitro or in vivo may provide insight into physiological processes and a number of human diseases. For example, it is known that changes in $Ca^{2+}$ concentration have a role in neuronal signaling, muscle contraction, and cell development and proliferation. Further, cellular processes such as gene expression, protein folding, metabolism and synthesis are controlled by different levels and kinetic properties of analyte signaling. Additionally, as diseases such as Alzheimer's disease, cancer, and lens cataract formation are known to be associated with altered $Ca^{2+}$ signaling, improved quantification and detection of such signals may provide valuable insight into the aforementioned diseases. Thus, detecting and quantifying changes in analytes that occur in cells or organisms may provide important insight into biological activities and diseases.

Specifically, for illustrative purposes, $Ca^{2+}$ binds many molecules, especially proteins, at different environments to regulate their functions. Currently more than 1000 calcium binding proteins are known in every kingdom, from mammalian to plants to bacteria. For example, calcium binds to calmodulin to trigger this protein to regulate over 100 processes in almost every compartment of the cell. Many calcium sensor receptors, growth factors, and cell adhesion molecules are directly regulated by calcium binding. $Ca^{2+}$ signal changes are used as one of the best ways to monitor neuron science, brain and behaviors. Therefore, accurate measurement of $Ca^{2+}$ concentration in a broad concentration range under in vitro or in vivo (both intracellular and extracellular) conditions by non-invasive techniques, without significantly disrupting cellular functions, is of paramount importance. As such, the constant $Ca^{2+}$ homeostasis results in local $Ca^{2+}$ variations.

Accordingly, there is always a need for an improved analyte sensor for quantifying and detecting analyte concentrations and changes thereof in both in vivo and in vitro systems and for probing the functionality of analyte binders and for methods of constructing and engineering new binding sites. Due to the importance of analytes in the physiology of biological and cellular processes, it is essential to develop analyte binding sites for use in proteins, e.g. fluorescent protein, and methods constructing such binding sites. Further, it is important to develop an analyte sensor that can detect changes of the analyte concentration in the microenvironment inside or outside of cells in real time. Such sensors, which can detect changes in microenvironments, are useful as probes of cellular events involving changes in such microenvironments due to movement of molecules in solution or the special location of molecules associated with cell membranes. It is to these needs among others that the present invention is directed.

BRIEF SUMMARY OF THE INVENTION

One aspect of this invention is an analyte sensor comprising an analyte-binding site and a host protein, which together produce a detectable signal when exposed to an analyte or a flux of analyte in its microenvironment. More particularly, the analyte sensor comprises a tailored analyte binding motif that binds an analyte and a host protein operatively linked to the analyte binding motif, wherein the binding of the analyte to the analyte binding motif produces a detectable change, and manipulation of the analyte binding motif manipulates the responsiveness of the sensor. For example, the analyte binding motif can be integrated or operatively linked into an optically active fluorescent host protein, such that analyte sensor produces a detectable change in fluorescence properties, e.g. emission spectra, based on the quantity of the analyte or flux thereof in the microenvironment. In another example, an analyte binding motif is integrated or operatively linked into a host protein with binding affinity to a fluorescent analyte such as a Lanthanide Series ion, such that the analyte sensor produces a detectable change. Preferably, the host protein is a fluorescent protein and the analyte is a metal ion. In one embodiment the sensor is able to detect an analyte concentration in the range from 0 to 20 mM in a microenvironment, such as for example, the cytosol or endoplasmic reticulum of a cell.

An analyte sensor illustrative of the present invention can be constructed by constructing a tailored analyte binding motif capable of responding to an analyte and operatively inserting the analyte binding motif into a host protein. Analyte binding sites typically have a primary structure, a secondary structure, in many cases a tertiary structure, and in some cases a quaternary structure, at least one of which can be tailored to the sensor to achieve a desired level of analyte sensitivity. That is, each of the primary structure, secondary structure, tertiary structure, and quaternary structures can be tailored to the sensor independently or in combination with one or more other structures to achieve a desired level of analyte sensitivity. In a preferred embodiment, the binding of the analyte to the analyte binding site of the sensor produces a detectable change and the manipulation of the analyte binding motif manipulates the responsiveness of the sensor.

The present invention also allows one to quantify an analyte by introducing a nucleotide sequence encoding a protein to an analyte sensor with a tailored analyte binding motif that is able to produce a detectable change upon excitation, expressing the protein, providing excitement to the analyte sensor, and then quantifying the detectable change. The protein can include a host protein. The emission intensity of the host protein, which preferably is a fluorescent protein, is relative to the quantity of analyte in a microenvironment.

The present invention also allows one to create a nucleic acid sequence for an analyte sensor comprising a tailored analyte binding motif sequence for an analyte binding peptide that produces a detectable change upon excitation and a host sequence for a host protein. In this nucleic acid sequence, the tailored binding motif sequence and the host protein sequence are operatively linked, and manipulation of the analyte binding motif sequence manipulates the responsiveness of the analyte sensor.

The analyte binding site can be constructed from a modified natural analyte binding site and, in the case where the analyte is $Ca^{2+}$, can comprise at least one calcium binding motif. Alternatively, the analyte binding site can be a novel site created from known parameters. In certain embodiments, the sensor also can comprise aromatic residues.

Depending on the analyte and host protein selected, the detectable change can be detectable from fluorescence spectroscopy or microscopy, NMR microscopy and/or Lanthanide Series sensitized energy transfer fluorescence spectroscopy. Other detection methods can be used as well, with the three methods mentioned above being preferred.

Another aspect of this invention is a method for creating a tailored analyte binding site through the use of a grafting method. The grafting method focuses on engineering and constructing an analyte binding motif by modifying the primary, secondary, tertiary, and/or quaternary structure of an identified binding site. In one example, a $Ca^{2+}$ binding site may be constructed from continuous binding motifs such as conserved calcium binding motifs from EF-hand proteins (EF-loop) using a grafting approach, which can involve criteria to obtain a preferred intrinsic metal-binding affinity for each calcium binding motif.

An illustrative method for constructing an analyte binding site using the grafting method comprises the steps of identifying an analyte binding peptide that binds an analyte with specificity, ascertaining at least a portion of a nucleic acid sequence encoding the analyte binding peptide, tailoring the nucleic acid sequence encoding the analyte binding peptide into an analyte binding site, identifying a host protein and a relevant portion of the nucleic acid sequence of the host protein, operatively linking the tailored nucleic acid sequence encoding the analyte binding peptide and the host protein nucleic acid sequence into an analyte binding motif sequence, and then expressing the analyte binding motif sequence, whereby the nucleic acid sequence encoding the analyte binding peptide is tailored so as to achieve the analyte binding motif with a desired specificity for the analyte. Preferably, the nucleic acid sequence encoding the analyte binding peptide is tailored to have specificity for the analyte over other analytes. Resultant proteins encoded by the analyte binding motif sequence are useful products of this invention.

As mentioned previously, analyte binding sites typically have a primary structure, a secondary structure, a tertiary structure, and a quaternary structure, each of which can be modified independently or in combination with others of the structures when tailoring of the nucleic acid sequence encoding the analyte binding peptide. For example, the primary structure can be tailored by inserting at least one codon into the nucleic acid sequence encoding the analyte binding peptide. Similarly, codons for charged amino acids can be inserted into the nucleic acid sequence encoding the analyte binding peptide.

One manner of tailoring the analyte binding site comprises selectively manipulating and adding helices, loops, bridges or linkers. Further, charged amino acids can be inserted into the amino acid sequence encoding the analyte binding peptide. Additionally, aromatic amino acids can be introduced into the amino acid sequence encoding the analyte binding peptide. It also is preferred to tailor the host protein amino acid sequence to achieve the analyte binding motif with a desired specificity for the selected analyte.

Another aspect of this invention is a method for creating a tailored analyte binding motif through the use of a computational approach in which a computational method for engineering and constructing an analyte binding motif de novo is based on optimal binding characteristics of an analyte with other moieties. In one embodiment, using established criteria for evaluating $Ca^{2+}$ binding data, a $Ca^{2+}$ binding site of desired sensitivity may be constructed by molecular modeling. For example, such computation approaches may be used to develop desired ion binding motifs based on parameters such as the metal's binding geometry, the folding of the fluorescent protein, the location of the charges on the fluorescent protein, the particular chromophores, and other criteria specific to the $Ca^{2+}$ binding data.

A general method for constructing an analyte binding motif using the computational approach comprises the steps of accessing a database that comprises structural data on analyte binding sites, generating at least one preliminary analyte binding site from the structural data, selecting an analyte binding site from the preliminary analyte binding sites, and constructing the analyte binding motif by tailoring the selected analyte binding site and operatively linking it with a host protein, wherein the analyte binding motif has a specificity for a selected analyte. Although the computational approach can be carried out by hand, it is much more efficient to use a computer.

Somewhat more specifically, an illustrative version of the computational approach comprises the steps of querying a database that comprises structural data on analyte binding sites using selected criteria relevant to the analyte binding motif, generating at least one preliminary analyte binding site from the database based on compatibility with the selected criteria, selecting an analyte binding site from the preliminary analyte binding sites based on optimal compatibility with the selected criteria, obtaining the nucleic acid sequence of the selected analyte binding site, tailoring the nucleic acid sequence of the selected analyte binding site, and operatively linking the nucleic acid sequence of the selected analyte binding site and a host protein sequence, whereby the nucleic acid sequence of the selected analyte binding site is tailored so to achieve the analyte binding motif having a desired specificity for the analyte.

An illustrative system for carrying out the computational approach comprises at least one database that comprises structural data on analyte binding sites, an algorithm for generating at least one preliminary analyte binding site from portions of the structure data using selected criteria relevant to the analyte binding motif and rating the preliminary analyte binding sites based on specificity for a selected analyte, and a computer for executing the algorithm so as to query the databases to generate the preliminary analyte binding sites. The algorithm generally is a relatively simple searching algorithm that will query the databases based on inputted criteria.

The structural data typically can comprise amino acid sequences, secondary structures, nucleic acid sequences, geometric parameters, electrostatic properties, and coordination properties of the analyte binding sites, such as in protein and gene banks. These data can be found in public and/or private databases, many of which are available over the Internet or through subscriptions. Other databases can be private databases compiled by researchers or the like.

In one embodiment of the computational approach, at least one preliminary binding site is generated based on random portions of the structural data. Further, a nucleic acid sequence encoding the preliminary binding sites can be generated from the structural data.

The host protein preferably is selected from the group consisting of green fluorescent protein, cyan fluorescent protein, yellow fluorescent protein, red fluorescent protein, gold fluorescent protein and combinations thereof. More specifically, the host fluorescent protein preferably is an Aequora-related protein. The analyte preferably is a transition metal ion, a Group IIA metal ion, or a Lanthanide Series ion. $Ca^{2+}$ is a preferred Group IIA metal ion, $Mn^{2+}$ and $Cd^{2+}$ are preferred transition metal ions, and all Lanthanide Series ions are preferred, such as $Tb^{3+}$, $Gd^{3+}$ and $Eu^{3+}$.

Once the analyte binding motif has been tailored and operatively linked into the fluorescent host protein, the analyte sensor may show responsiveness to analyte dependant fluorescence variations. The responsiveness of analyte sensors is caused by the interaction of the fluorescent protein with the analyte binding motif, which then displays fluorescence properties proportional to the analyte concentration or flux thereof in the microenvironment. The interaction between the analyte and the fluorescent protein results in a detectable change that may be analyzed in real-time to probe the microenvironment.

In use and application, the analyte sensor may be used to detect and quantify the analyte concentration and flux thereof in a sample as a non-ratiometric dye. More particularly, the analyte sensor is inserted into the sample, the sample then is excited by radiation, the fluorescence from the sample then is measured using an optical device, and the fluorescence or flux thereof then is analyzed to quantify or detect the analyte concentration in the sample.

These features, and other features and advantages of the present invention, will become more apparent to those of ordinary skill in the relevant art when the following detailed description of the preferred embodiments is read in conjunction with the appended drawings in which like reference numerals represent like components throughout the several views.

BRIEF DESCRIPTION OF THE FIGURES

FIG. 2A illustrates the fluorescent emission spectra of Sensor-G1 in the absence and presence of $Ca^{2+}$. FIG. 2B illustrates a curve-fitting of $Ca^{2+}$ titration in 10 mM Tris, 1 mM DTT, and pH7.4.

DETAILED DESCRIPTION OF THE PREFERRED EMBODIMENTS

Figure 1:
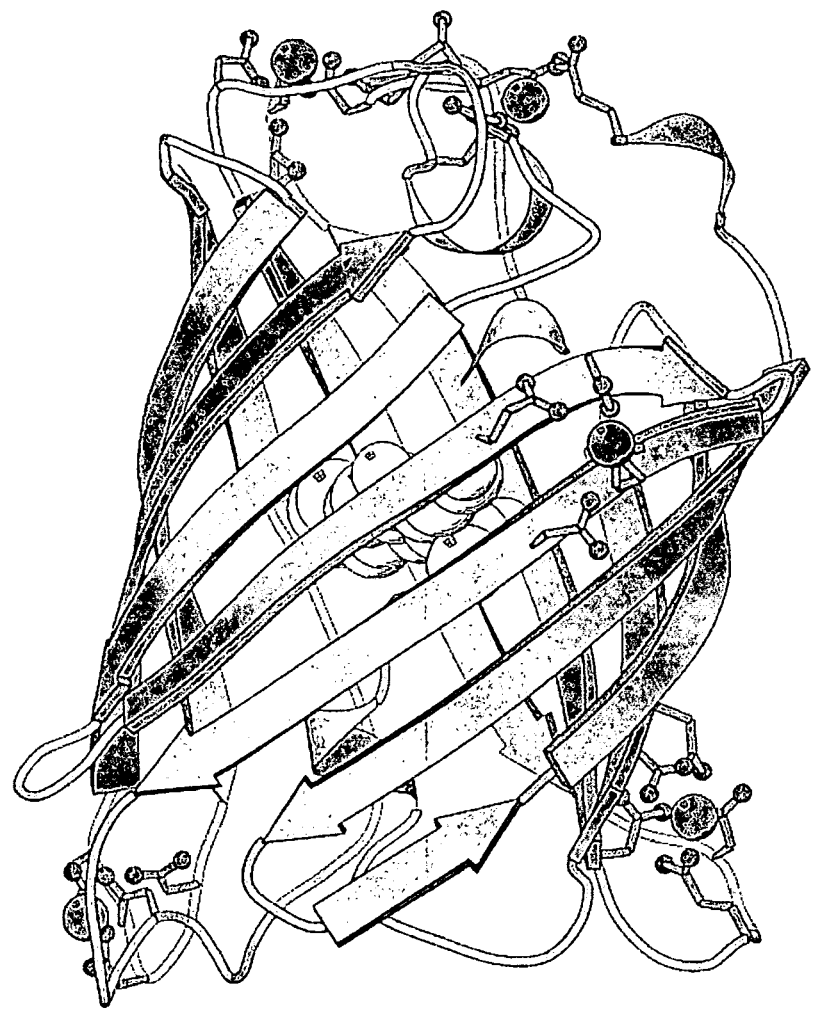
FIG. 1 is a 3-dimensional structure of an exemplary GFP designed with a computational created $Ca^{2+}$ binding site (the spherical ball).

This invention is an analyte sensor that utilizes fluorescence to detect and quantify an analyte. The analyte sensor includes at least one analyte binding motif operatively linked into a host protein having fluorescent properties, resulting in a fluorescent sensor. This host protein is selected so that the excitation spectrum of the host protein produces an emission spectrum that may be measured to detect or determine the concentration or change in concentration of a particular analyte. More particularly, the binding of the analyte to the analyte binding motif of the host protein produces a detectable change in the emission spectra produced by the analyte sensor. Further, as the analyte sensor may be targeted or directed to any specifical cellular compartments and may be genetically turned on (and off), this invention allows for detection and quantification of an analyte in a microenvironment, such as, for example, the cytosol or, even more specifically, specific areas of a cell such as the endoplasmic reticulum.

This invention further contemplates the use of grafting or tailoring methods for constructing an analyte binding motif, such as by operatively linking a tailored nucleic acid sequence encoding an analyte binding peptide and a host protein nucleic acid sequence into an analyte binding motif sequence. This invention additionally contemplates the use of computational approaches for constructing an analyte binding motif, such as by using an algorithm and accessing databases having structural data on analyte binding sites and generating a suitable analyte binding site from the structural data using selected criteria relevant to a desired analyte binding motif.

DEFINITIONS

In this specification, various terms are defined as follows:

"Analytes" are atoms, molecules or ions that can bind to proteins or peptides. An analyte may bind reversibly or irreversibly and such a bond may be covalent or non-covalent. While $Ca^{2+}$ is used in preferred embodiments of this invention as an exemplary analyte, it is understood that analytes suitable with this invention include, but are not limited to metal ions including Group IIA metal ions, transition metal ions, and Lanthanide Series ions.

"Bonds," "bonding," and "linkages" are ionic, covalent, or noncovalent attractions of all types.

"Binding site" refers to any section of a peptide or protein involved in forming bonds with an analyte.

"Binding motif" is part of a binding site, often in a larger protein. The term binding site may be used interchangeably with the term binding motif and vice versa.

"Chemical reactions" can include the formation or dissociation of ionic, covalent, or noncovalent structures through known means. Chemical reactions can include changes in environmental conditions such as pH, ionic strength, and temperature.

"Conformation" is the three-dimensional arrangement of the primary, secondary, and tertiary structures of a molecule, and in some instances the quaternary structure of a molecule, including side groups in the molecule; a change in conformation occurs when the three-dimensional structure of a molecule changes. A conformational change may be a shift from an alpha-helix to a beta-sheet or a shift from a beta-sheet to an alpha-helix.

"Control sequences" are polynucleotide sequences that are necessary to effect the expression of coding and non-coding sequences to which they are ligated. Such control sequences can include a promoter, a ribosomal binding site, and a transcription termination sequence. The term "control sequences" is intended to include, at a minimum, components whose presence can influence expression and can also include additional components whose presence is advantageous. For example, leader sequences and fusion partner sequences are control sequences.

"Covalently coupled" refers to a covalent bond or other covalent linkage between two moieties.

"Detectable changes" or "responsiveness" means any response of a protein to its microenvironment. Such detectable changes or responsiveness may be a small change or shift in the orientation of an amino acid or peptide fragment of the sensor polypeptide as well as, for example, a change in the primary, secondary, or tertiary structure of a polypeptide, and in some instances the quaternary structure of a polypeptide, including changes in protonation, electrical and chemical potential and or conformation.

"Fluorescent protein" is any protein capable of light emission when excited with an appropriate electromagnetic energy. Fluorescent proteins include proteins having amino acid sequences that are either natural or engineered, such as the fluorescent proteins derived from *Aequorea victoria* fluorescent proteins.

"Fluorescence" is one optical property of an optically active polypeptide or protein that can be used as the means of detecting the responsiveness of the sensor of the invention.

"Fluorescent properties" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy.

A "measurable difference" in any fluorescent properties between the active and inactive states suffices for the utility of the fluorescent protein substrates of the invention in assays for activity. A measurable difference can be determined by measuring the amount of any quantitative fluorescent property, e.g., the fluorescence signal at a particular wavelength or the integral of fluorescence over the emission spectrum.

"Operatively inserted" or "linked" refers to a juxtaposition wherein the components so described are in a relationship permitting them to function in their intended manners. A control sequence operatively linked to a coding sequence is ligated such that expression of the coding sequence is achieved under conditions compatible with the control sequences.

"Nucleic acid sequences" include "polynucleotides," which are a polymeric form of nucleotides at least 10 bases in length. The nucleotides can be ribonucleotides, deoxynucleotides, or modified forms of such nucleotide. This term can refer to single and double stranded forms of DNA or RNA.

"Peptides" are polymers of amino acid residues that are connected through amide bonds. As defined herein, peptides are inclusive of both natural amino acids and unnatural amino acids (e.g. beta-alanine, phenylglycine, and homoarginine). While amino acids are alpha-amino acids, which can be either of the L-optical isomer or the D-optical isomer, the L-optical isomers are preferred. Such amino acids can be commonly encountered amino acids that are not gene-encoded, although preferred amino acids are those that are encodable.

"Responsive" is intended to encompass any response of a polypeptide or protein to an interaction with an analyte.

"Substantially the same amino acid sequences" are amino acid sequences that are largely the same and have similar functional activities. For example, two amino acid sequences are substantially the same with at least 80% identical overlap and with similar three-dimensional structural motifs.

"Target peptides" are peptides that can bind to a binding protein. The target peptide may be a subsequence of a peptide that binds to the binding protein.

Unless otherwise defined, all technical and scientific terms used herein have the same meaning as commonly understood by one of ordinary skill in the art to which this invention pertains. Although methods and materials similar or equivalent to those described herein can be used in the practice and testing of the present invention, suitable methods and materials are described below. In addition, the materials, methods, and examples are illustrative only and not intended to be limiting.

Preferred Embodiments

In an embodiment of this invention, the analyte sensor comprises an analyte binding site and a host fluorescent protein, which together produce an optically detectable signal when exposed to an analyte or a flux of analyte in its microenvironment. The basic analyte sensor comprises:

a) a tailored analyte binding motif that binds an analyte; and b) a host protein operatively linked to the analyte binding motif, wherein the binding of the analyte to the analyte binding motif produces a detectable change. For example, the analyte binding motif is integrated or operatively linked into an optically active fluorescent host protein, such that the analyte sensor produces a detectable change in fluorescence properties, e.g. emission spectra, based on the quantity of the analyte or flux in concentration of the analyte in the microenvironment. In another example, an analyte binding motif is integrated or operatively linked into a host protein with binding affinity to a fluorescent analyte such as $Tb^{3+}$, such that the analyte sensor produces a detectable change based on the quantity of the analyte or flux in concentration of the analyte in the microenvironment. Preferably, the quantity change or flux produces a detectable change.

A preferred illustrative embodiment of the analyte sensor comprises a host protein that is a fluorescent protein and an analyte that is a metal ion. The sensor preferably is able to detect any analyte concentration or flux, and more preferably an analyte concentration in the range from 0 to 20 mM in a microenvironment, such as for example the cytosol or endoplasmic reticulum of a cell.

The preferred analyte sensor can be constructed by first constructing a tailored analyte binding motif capable of responding to an analyte and second operatively inserting the analyte binding motif into a host protein. Analyte binding sites typically have a primary structure, a secondary structure, and a tertiary structure in most cases and in some cases a quaternary structure, at least one of which can be tailored to the sensor to achieve a desired level of analyte sensitivity. That is, each of the primary structure, the secondary structure, the tertiary structure, and if present, the quaternary structure can be tailored to the analyte sensor independently or in combination with one or more others of the structures to achieve a desired level of sensitivity for the sensor relative to the analyte. For example, the binding of the analyte to the analyte binding motif preferably produces a detectable change (fluorescence) and the manipulation of the analyte binding motif manipulates the responsiveness of the sensor.

The analyte sensor also allows the quantification of an analyte by introducing a nucleotide sequence for a protein to an analyte sensor with a tailored analyte binding motif that is able to produce a detectable change upon excitation, expressing the protein, providing excitement to the analyte sensor, and then quantifying the detectable change. Preferably, the protein can include a host protein, which preferably is a fluorescent protein, whose emission intensity is relative to the quantity of analyte in a microenvironment.

Additionally, a nucleic acid sequence can be created for an analyte sensor comprising a tailored analyte binding motif sequence for an analyte binding peptide that produces a detectable change upon excitation and a host sequence for a host protein. In this nucleic acid sequence, the tailored binding motif sequence and the host protein sequence are operatively linked, and manipulation of the analyte binding motif sequence manipulates the responsiveness of the analyte sensor.

One method for creating a tailored analyte binding motif is through the use of a novel grafting method. The grafting method focuses on engineering and constructing an analyte binding motif by modifying the primary, secondary, tertiary, and/or quaternary structure of an identified binding site. In one example, a $Ca^{2+}$ binding motif may be constructed from continuous binding motifs such as conserved calcium binding motifs from EF-hand proteins (EF-loop) using a grafting method, which can involve criteria to obtain a preferred intrinsic metal-binding affinity for each calcium binding motif.

A preferred illustrative method for constructing an analyte binding motif using the grafting method comprises first identifying an analyte binding peptide that binds an analyte with specificity and then ascertaining at least a portion of a nucleic acid sequence encoding the analyte binding peptide. Once this is accomplished, the nucleic acid sequence encoding the analyte binding peptide is tailored into an analyte binding site. After the tailoring is completed, a host protein is selected and a relevant portion of the nucleic acid sequence of the host protein is identified, and the tailored nucleic acid sequence encoding the analyte binding peptide is operatively linked with the host protein nucleic acid sequence into an analyte binding motif sequence. Finally, the analyte binding motif sequence is expressed. In this method, the nucleic acid sequence encoding the analyte binding peptide is tailored so as to achieve the analyte binding motif with a desired specificity for the analyte. Preferably, the nucleic acid sequence encoding the analyte binding peptide is tailored to have specificity for the analyte over other analytes. Resultant proteins encoded by the analyte binding motif sequence are useful products of this invention.

As mentioned previously, analyte binding sites typically have a primary structure, a secondary structure, in most cases a tertiary structure, and in some cases a quaternary structure, each of which can be modified independently or in combination with others of the structures when tailoring of the nucleic acid sequence encoding the analyte binding peptide. For example, the primary structure can be tailored by inserting at least one codon into the nucleic acid sequence encoding the analyte binding peptide. Similarly, codons for charged amino acids can be inserted into the nucleic acid sequence encoding the analyte binding peptide.

The analyte binding site can be tailored by selectively manipulating and adding helices, loops, bridges or linkers, among other methods. Charged amino acids can be inserted into the amino acid sequence encoding the analyte binding peptide and or aromatic amino acids can be introduced into the amino acid sequence encoding the analyte binding peptide.

Another method for creating a tailored analyte binding motif is through the use of a computational approach in which a computational method for engineering and constructing an analyte binding motif de novo is based on optimal binding characteristics of an analyte with other moieties. In one illustrative embodiment, using established criteria for evaluating $Ca^{2+}$ binding data, a $Ca^{2+}$ binding site of desired sensitivity may be constructed by molecular modeling. For example, such computation algorithms may be used to develop desired ion binding motifs based on parameters such as the metal's binding geometry, the folding of the host protein, the location of the charges on the fluorescent protein, the particular chromophores, and other criteria specific to the $Ca^{2+}$ binding data.

The computational approach can be used to construct an analyte binding motif by accessing public and or private databases that comprise structural data on analyte binding sites, generating at least one preliminary analyte binding site from the structural data based on certain previously selected criteria, selecting one or more suitable analyte binding sites from the preliminary analyte binding sites, and constructing the analyte binding motif by tailoring the selected analyte binding site and operatively linking it with a host protein, keeping in mind that the analyte binding motif preferably has a specificity for a selected analyte. The structural data typically can comprise amino acid sequences, secondary structures, nucleic acid sequences, geometric parameters, electrostatic properties, and coordination properties of the analyte binding sites, such as in protein and gene banks.

An illustrative version of this computational approach is the computerized (or otherwise automated) querying of one or more databases that comprise structural data on analyte binding sites using selected criteria relevant to the analyte binding motif, generating at least one preliminary analyte binding site from the database information based on compatibility with the selected criteria, and selecting one or more suitable analyte binding sites from the preliminary analyte binding sites based on optimal compatibility with the selected criteria. Once a suitable analyte binding site is selected, the nucleic acid sequence of the selected analyte binding site is obtained, tailored, and operatively linked with a host protein sequence, whereby the nucleic acid sequence of the selected analyte binding site is tailored so to achieve the analyte binding motif having a desired specificity for the analyte. In one embodiment of the computational approach, at least one preliminary binding site is generated based on random portions of the structural data. Further, a nucleic acid sequence encoding the preliminary binding sites can be generated from the structural data. The computational approach also can be used to express the analyte binding motif.

The computational approach can be performed on or by a system comprising at least one database that comprises the structural data on analyte binding sites, an algorithm for generating the preliminary analyte binding sites from portions of the structural data using selected criteria relevant to the analyte binding motif and rating the preliminary analyte binding sites based on specificity for a selected analyte, and a computer for executing the algorithm so as to query the databases to generate the preliminary analyte binding sites. The algorithm generally is a relatively simple searching algorithm that will query the databases based on inputted criteria.

Once the analyte binding motif has been tailored and operatively linked into the host protein, the analyte sensor may show responsiveness to analyte dependant fluorescence variations. The responsiveness of the analyte sensor is caused by the interaction of the host protein with the analyte binding motif, which then may display fluorescence properties proportional to the analyte concentration or flux. When the host protein is a fluorescent protein, such responsiveness is thought to be caused by changes in the orientation and protonation of the chromophore of the fluorescent protein. The interaction between the analyte and the host protein may result in a shift in the emission spectra, quantum yield, and/or extinction coefficient, which may be quantitatively analyzed in real-time to probe the microenvironment.

In use and application, the analyte sensor may be used to detect and quantify the analyte concentration and flux thereof in a sample as a non-ratiometric dye. More particularly, the analyte sensor is inserted into the sample, the sample then is excited by radiation, the fluorescence from the sample then is measured using an optical device, and the fluorescence or flux thereof then is analyzed to quantify or detect the analyte concentration in the sample. In order to analyze the sample, it may be necessary to generate a standard curve based on the fluorescence generated from known analyte concentrations. Specifically, the fluorescence signal of the analyte sensor is compared to the fluorescence of the standard curve so as to determine the concentration of analyte in the sample.

Fluorescent Proteins

Fluorescent proteins are one class of preferred host protein for this invention and include an array of fluorescent proteins including those related to *Aequorea*. Suitable fluorescent proteins should have a useful excitation and emission spectra and may have been engineered from naturally occurring *Aequorea Victoria* green fluorescent proteins (GFPs). Such modified GFPs may have modified nucleic acid and protein sequences and may include elements from other proteins. The cDNA of GFPs may be concatenated with those encoding many other proteins—the resulting chimerics are often fluorescent and retain the biochemical features of the partner proteins. Mutagenesis studies have produced many GFP mutants, some have shifted wavelengths of excitation or emission. Such proteins also are included in the invention.

One specific type of fluorescent protein that may be used with this present invention is a mutant enhanced green fluorescent protein (EGFP), which has a 30% increase in fluorescence over conventional green fluorescent proteins. Similar to GFPs, EGFP is comprised of 238 amino acids, is autocatalytic, and has chromospheres almost completely buried in the center of the 11-stranded β-barrel. The wild-type absorbance/excitation peak is at 395 nm with a minor peak at 475 nm (the edge of the red spectra band), and has extinction coefficients of roughly 30000 and 7000 $M^{-1}$ $cm^{-1}$, respectively. The emission peak is at 508 nm. Excitation at 395 nm leads to decrease over time of the 395 nm excitation peak and a reciprocal increase in the 475 nm excitation band. A change in protonation is likely responsible for different optical properties. This presumed photoisomerization effect is especially evident with irradiation of GFP by UV light.

While GFPs, which are proteins that emit green shifted spectra, are a preferred fluorescent protein, any fluorescent protein with chromophore sites and in which the activated conformation emits distinct fluorescent patterns from the unactivated conformation may be used in the invention. Other fluorescent proteins include blue fluorescent proteins (BFPs), which emit blue shifted spectra; yellow fluorescent proteins (YFPs), which emit yellow shifted spectra; cyan fluorescent proteins (CFPs), which emit a greenish-blue shifted spectra; gold fluorescent proteins (GoFPs), which emit goldish shifted spectra; and red fluorescent proteins (RFPs), which emit a reddish shifted spectra. Such fluorescent proteins have been isolated and extracted from jellyfish, *Aequorea victoria*, the sea pansy, *Renilla reniformis*, and *Phialidium gregarium*. One of ordinary skill in the art can select a fluorescent host protein based on preferences without undue experimentation. Further, preferred embodiments of the present invention may include any array of modifications on the basic structure of the fluorescent sensors including the introduction of other reporter genes, which may cause variations in the emissions spectrum.

Other Proteins

Other proteins may be used as host proteins for this invention. For example, any protein with aromatic residues, such as Trp, Typ, or Phe, are able to serve as preferred host proteins. An aromatic residue can be added in any protein that does not have any aromatic residues to facilitate the energy transfer mechanism. Such an example includes CD2, which has several aromatic residues. Further, $Eu^{3+}$ with fluorescent properties are another class of preferred host proteins. These other proteins need not be fluorescent proteins or have fluorescent properties. Specifically, their capability to bind fluorescent ions such as $Tb^{3+}$ may be created by the present invention. Preferably, host proteins are able to tolerate the addition of the analyte binding motif without substantial disruption to its structure. One of ordinary skill in the art can select a host protein based on preferences without undue experimentation.

Analyte Binding Motifs

The sensitivity of the analyte binding motif may vary the sensitivity of the analyte sensor. Specifically, as affinity and sensitivity of the analyte binding motif may be modified, the analyte sensor may be used to monitor analyte signaling in cells with different levels of analyte content and sensitivity. Such introductions of analyte binding motifs results in an analyte sensor that is able to detect and quantify the analyte without undue interference from other extraneous ions.

The analyte binding motif of the present invention may be constructed using at least two methods:

(1) A grafting method in which the analyte binding motif with a selectivity and affinity for an analyte is engineered and constructed selectively by varying the primary, secondary, tertiary, and/or quaternary structure of an identified binding site.

(2) A computational design approach in which that the analyte binding motif with a selectivity and affinity for an analyte is engineered and rationally designed de novo based on optimal binding characteristics of analyte with other moieties.

1. The Grafting Method

The grafting method focuses on engineering and constructing an analyte binding motif by modifying the primary, secondary, tertiary, and/or quaternary structure of an identified binding site. By selectively manipulating the structure of the binding site, it is possible to obtain an analyte binding motif that can be engineered into a protein, e.g. fluorescent protein, without significantly denaturing the protein. Using the grafting method, it is possible to achieve a binding site that has a stronger preference for one analyte over another analyte. Such modifications may allow for improved binding affinity and responsiveness of the analyte binding motif.

Initially, an identified binding site for use with the grafting method may be any continuous sequence motif that has some affinity for an analyte. Such binding sites may derive from either known binding peptides such as an individual EF-hand motif or from short fragments that have demonstrated the ability to bind specific analytes. Such peptides may be highly conserved in nature and prevalent throughout nature or may be unnatural but known to have an affinity for a particular analyte. One of ordinary skill in the art is able to identify binding sites with affinity for an analyte without undue experimentation.

Once the binding site has been identified, the primary structure of the analyte binding site may be altered and tuned to achieve an analyte binding motif with an improved sensitivity and responsiveness. For example, more charged ligand residues such as aspartate and glutamate may be engineered by inserting codon(s) into the analyte binding site so as to tune the responsiveness of the site or the host protein (e.g. by inducing a larger change in the chromophore environment). Further other mutations to the primary structure include removing or adding amino acids to change properties such as flexibility or rigidity of the motif. Adding or removing amino acids from the binding motif alters the primary structure of the binding site.

The secondary structure of the analyte binding site, that is the spatial arrangement of amino acids residues that are near one another in linear sequence, may be modified to tune the sensitivity and responsiveness of the analyte binding motif. The residues on the site itself, the flanking or the neighboring helices may be modified by changing properties such as hydrophobicity, salt bridges, secondary structure propensity (e.g. helicity, and β-sheets), and charge interactions with different amino acids, which all may inherently change the secondary structure.

The tertiary structure of the analyte binding site may be modified to further tune the sensitivity and responsiveness of the analyte binding motif. The affinity of the analyte binding site for the analyte may be varied by selectively manipulating and adding helices, loops, bridges and/or linkers. In fact, such variations in tertiary structure may add stability and affinity by increasing secondary structure propensity, adding charge interaction of the side chains, and by stabilizing the analyte binding coordination chemistry. As such, it may be possible to increase or decrease the binding affinity of the continuous binding motif by tuning the tertiary structure of the analyte binding site. A close distance from aromatic residues to the analyte binding site may be achieved by tuning the tertiary structure, which can allow fluorescent properties dependant on the energy transfer from aromatic residues to the analyte, such as $Tb^{3+}$.

Further, the quaternary structure of the analyte binding site may be modified to tune the sensitivity and responsiveness of the analyte binding motif. It is possible to tune the structure so that the host protein may form oligomers (such as dimer or trimers) so as to enhance responsiveness. Such tuning may be accomplished by increasing or altering metal binding properties and properties such as the flexibility of the binding motif and can improve cooperatively like that shown in EF-hand motifs in calmodulin. In addition, if the protein does not have aromatic residues, the formation of hetromers with proteins having such residues can produce responsiveness, e.g. through an energy transfer fluorescent signal of the analyte.

One method of directly altering the primary, secondary, and/or tertiary structure of the analyte binding site is by altering the charges in the motif. As the charges in any binding motif have a significant role in the structure of the motif, changing the charges or charge ratio may have significant impact on the structure of the motif. More importantly, as the charged side chains exhibit a strong influence on the analyte binding affinity, even though they are not directly involved as ligands, the variation of these chains results in variations in analyte binding affinities and selectivity. An analyte binding motif may have stronger affinities to and better selectivity for a desired analyte over a competitive analyte by designing or modifying the motif, e.g., changing the number of charged ligand residues to form analyte binding pockets. For example, the analyte binding affinity of the analyte binding motif may be varied by changing the charged side chains that are present on the analyte binding motif and or the neighboring environment. The replacement of charged residues such as aspartate or glutamate with a residue such as alanine may dramatically reduce the binding affinity for the analyte by up to 100 times.

Thus, by varying the primary, secondary, tertiary, and/or quaternary structure of the analyte binding site, it is possible to achieve an analyte binding motif with desired specificity and affinity.

2. The Computational Design Approach

The computational design approach focuses on designing an analyte binding motif de novo. This design approach focuses on using an algorithm to construct and engineer an optimal binding site. The computational design approach comprises the following steps:

(1) accessing one or more databases having structural data on analyte binding sites;

(2) generating one or more preliminary analyte binding sites from portions of the structural data;

(3) selecting rationally one or more suitable analyte binding sites from the generated preliminary binding sites; and (4) creating an analyte binding motif by tailoring and tuning the selected analyte binding site.

The analyte binding motif may be incorporated into a protein, e.g. a fluorescent protein. Further, such a method may be used to alter analyte binding properties of proteins and generate new materials with various ion binding affinities.

More particularly, the method involves searching and accessing public and or private databases for preferred components of an analyte binding site. Such databases that may be searched for the criteria or components may include public domain banks (e.g. NBCI or PubMed) or knowledge banks such as protein data banks (e.g. Cambridge Data Bank). Further, the database could include structural data from analyte binding proteins whose structures have been characterized previously. One of ordinary skill in the art can identify databases and sources of material for databases suitable with this invention. Use of a computer obviously would greatly speed up the searching and is preferred.

These databases may be used to provide structural analysis of one to several thousand different small molecules or analytes that bind to a protein. Such analysis may include local coordination properties, types of residues or atoms commonly used to bind a desired analyte, chemical features (e.g. pKa or changes), the number of charged residues on a site, and the range or deviation of the known binding sites. Further, such analysis may include the environment, such as types of atoms, residues, hydrophobicity, solvent accessibility, shapes of the metal binding sites, electrostatic potentials, and the dynamic properties (e.g. B-factors or the order factors of the proteins) of the binding sites. Such analysis also may include whether binding site for a particular analyte is a continuous or discontinuous binding site.

Once preliminary analyte binding sites are found, using the structural data and analysis, one or more suitable analyte binding sites may be generated based on rational factors. Specifically, different search algorithms may be used to generate potential analyte binding sites based on other key features in addition to, for example, the geometric descriptors. These key features include the properties of the original residues in the fluorescent protein, ligand positions that are essential to protein folding, the number of the charged residues and their arrangement and number of water molecules in the coordination shell. The hydrogen bond network and the electrostatic interactions with the designed ligand residues also can be evaluated. Furthermore, the protein environments of analyte binding sites can be analyzed according to solvent accessibility, charge distribution, backbone flexibility, and properties of fluorescent proteins and distances to optimal sites such as for example chromophores. Thus, one of ordinary skill in the art may rationally select a binding site based on desired parameters.

Once the analyte binding sites are generated, a site may be tailored using two complementary approaches of grafting and computational design. First, as discussed above, the analyte binding site may be tailored using a grafting method in which the primary, secondary, tertiary, and/or quaternary structures are tuned. Second, the analyte binding site may be tailored using a computational design approach. It is understood that one or both of these approaches may be used to tailor the binding site.

Referring now more particularly to the computational design approach, this approach includes modifying the analyte binding site by modifying residues in the scaffold of the analyte binding site. In one embodiment, a geometric description of the ligands around an analyte, a three-dimensional structure of the backbone of proteins, and a library of sidechain rotamers of amino acids (or atoms from the main chain) can identify a set of potential metal-binding sites using a computer. Using the geometric description of a particular analyte site, key ligand residues are carefully placed in the amino acid sequence to form the metal (analyte) binding pocket. This binding pocket can be created automatically by the computer algorithm according to the geometric description and the user's preferred affinity.

The created potential analyte binding sites can be optimized and tuned to specification. A backbone structure of the analyte binding site with different degrees of flexibility may be used according to the need or the flexibility of the analyte binding motif. The designed analyte binding sites are further filtered and scored based on the local factors, which may include the shape of the analyte binding sites, locations, charge numbers, dynamic properties, the number of mutation needed, solvent accessibility, and sidechain clashes.

Stronger analyte binding affinities of the designed sites may be developed based on several modeled factors that contribute to analyte affinity. For example, the number of ligand residues is a factor to directly chelate a specific analyte. In some cases, in order to have a strong analyte affinity with a $K_d$ necessary to measure an analyte concentration, it is necessary to include residues from the protein frame for optimal analyte binding. In other cases, the number of charged residues is able to change analyte affinity. In other cases, the ligand type is a factor as the binding preferences of a chelate may depend on the particular ligand type. Other factors, such as negatively charged environments, may contribute to the binding affinity of an analyte binding protein and can be taken into account without undue experimentation.

Once the analyte binding motif has been designed, it may be coupled the functional protein. Preferably, the analyte binding motif is stabilized within the protein and does not effect the function of protein.

An illustrative version of this computational approach is the computerized (or otherwise automated) querying of one or more databases that comprise structural data on analyte binding sites using selected criteria relevant to the analyte binding motif, generating at least one preliminary analyte binding site from the database information based on compatibility with the selected criteria, and selecting one or more suitable analyte binding sites from the preliminary analyte binding sites based on optimal compatibility with the selected criteria. Once a suitable analyte binding site is selected, the nucleic acid sequence of the selected analyte binding site is obtained, tailored, and operatively linked with a host protein sequence, whereby the nucleic acid sequence of the selected analyte binding site is tailored so to achieve the analyte binding motif having a desired specificity for the analyte. In one embodiment of the computational approach, at least one preliminary binding site is generated based on random portions of the structural data. Further, a nucleic acid sequence encoding the preliminary binding sites can be generated from the structural data. The computational approach also can be used to express the analyte binding motif.

The computational approach can be performed on or by a system comprising at least one database that comprises the structural data on analyte binding sites, an algorithm for generating the preliminary analyte binding sites from portions of the structural data using selected criteria relevant to the analyte binding motif and rating the preliminary analyte binding sites based on specificity for a selected analyte, and a computer for executing the algorithm so as to query the databases to generate the preliminary analyte binding sites. The algorithm generally is a relatively simple searching algorithm that will query the databases based on inputted criteria.

Selecting Analyte Binding Sites in a Fluorescent Host Protein

The analyte binding motifs may be selectively introduced into numerous sites of a host protein without substantially impairing its secondary structure. A number of methods for identifying insertion sites in proteins and fluorescent proteins, such as GFP, YFP, CFP, and RFP are known in the art, including, for example, site directed mutagenesis, insertional mutagenesis, and deletional mutagenesis. Other methods, including the one exemplified below and in the Examples, are known or easily ascertained by one skilled in art.

The sites of the fluorescent protein that can tolerate the insertion of an analyte binding motif also may be determined and identified by gene manipulation and screening. By generating mutant proteins and by manipulating the DNA sequence, it is possible to obtain a variety of different insertions, which then may be screened to determine whether the protein maintains its intrinsic activities. Preferably, sites that remove or interfere with the intrinsic fluorescence of the fluorescent protein are not optimal and may be screened out. Variants identified in this fashion reveal sites that can tolerate insertions while retaining fluorescence.

The preferred analyte binding motifs for use with fluorescent proteins may be selected by considering five criteria so to as optimize the local properties of the metal binding site, the fluorescent protein, and the protein environment. First, the geometry of the analyte binding motif should have relatively minor deviations from the desired pentagonal geometry. Second, negatively charged residues should be varied by no more than 3-5 charges according to the desired affinity for calcium ($K_d$). Third, the analyte binding sites should be in the positions close to the "chromophore-sensitive locations" as these sites result in greater chromophore signal emission. Fourth, the analyte binding site should be selected so as to minimize the mutations to the fluorescent protein. Fifth, the residues from the loops between the secondary structures with good solvent accessibility are desired for both the folding of the protein and the fast kinetics required for the sensor.

The mutation or the introduction of the analyte binding motif should not substantially interfere with the synthesis and folding of the fluorescent protein. More particularly, the introduction of the analyte binding motif does not interfere with either posttranslational chromophore formation or intermolecular interactions required for stabilizing the chromophores and folding of the protein frame. Furthermore, the introduced side chain should not be overpacked and should not clash with the protein frame. The direct use of chromophore residues as binding sites is not preferred but is within the scope of this invention.

Amino Acid and Nucleic Acid Sequences

The amino acid and nucleic acid sequences encoding the fluorescent sensor encode at least one analyte binding motif and the fluorescent protein. Preferably, at least one analyte binding motif and the fluorescent protein are operatively connected such that the fluorescence sensor may emit a fluorescence signal dependant upon the microenvironment. It is understood by those with ordinary skill in the art that it is unnecessary to provide herein the entire sequence of host proteins or of analyte binding motifs, as minor variations in the nucleic sequences would exhibit very little, if any, effect on the function of the protein.

While it is understood that numerous analyte sensors may be constructed using this invention, one analyte sensor has the following amino acid sequence (G1)

(SEQ ID NO: 1)
MGSSHHHHHHSSGLVPRGSHMASMTGGQQMGRGSGPSRMVSKGEELFTGV

VPILVELDGDLNGHKFSVSGEGEGDATYGKLTLKFICTTGKLPVPWPTLV

TTLTYGVQCFSRYPDHMKQHDFFKSAMPEGYVQERTIFFKDDGNYKTRAE

VKFEGDTLVNRIELKGIDFKEDGNILGHKLEYNYNSHNVYIMADKQKNGI

KVNFKIRHNIEEEEIREAFRVFDKDGNGYISAAELRHVMTNLDGSVQLAD

HYQQNTPIGDGPVLLPDNHYLSTQSALSKDPNEKRDHIVLLEFVTAAGIT

LGMDELYK

Another analyte sensor has the following amino acid sequence (G2)

(SEQ ID NO: 2)
MGSSHHHHHHSSGLVPRGSHMASMTGGQQMGRGSGPSRMVSKGEELFTGV

VPILVELDGDLNGHKFSVSGEGEGDATYGKLTLKFICTTGKLPVPWPTLV

TTLTYGVQCFSRYPDHMKQHDFFKSAMPEGYVQERTIFFKDDGNYKTRAE

VKFEGDTLVNRIELKGIDFKEDGNILGHKLEYNYNSHNVYIMADKQEEEI

REAFRVFDKDGNGYISAAELRHVMTNLKNGIKVNFKIRHNIEDGSVQLAD

HYQQNTPIGDGPVLLPDNHYLSTQSALSKDPNEKRDHIVLLEFVTAAGIT

LGMDELYK

Another analyte sensor in which the host protein is CD2 has two mutations of N15D and N17D has the following amino acid sequence (SEQ ID NO: 3)
RDSGTVWGALGHGIDLDIPNFQMTDDIDEVRWERGSTLVAEFKRKMKPFLK

SGAFEILANGDLKIKNLTRDDSGTYNVTVYSTNGTRILNKALDIRILE

Another analyte sensor with a similar sequence has five mutations of F21E, V78N, V80E, L89D, and K91D (SEQ ID NO: 4 with the mutation K91D instead of K91I). One of ordinary skill in the art may readily derive the nucleic acid sequence from amino acid sequences.

Measuring Fluorescence

Suitable methods for measuring fluorescence of samples are known and understood by those with ordinary skill in the art. Preferred methods for measuring fluorescence should be capable of measuring the fluorescence of the ion species and determining the ion concentration. Some representative known methods of performing assays on fluorescent materials are described in, e.g., Lakowicz, J. R., Principles of Fluorescence Spectroscopy, (Plenum Press 1983); Herman, B., Resonance Energy Transfer Microscopy, Fluorescence Microscopy of Living Cells in Culture, Part B, Methods in Cell Biology, vol. 30, pp. 219-243 (ed. Taylor, D. L. & Wang, Y.-L., Academic Press 1989); Turro, N. J., Modern Molecular Photochemistry, pp. 296-361 (Benjamin/Cummings Publishing, Inc. 1978). Further, there are numerous commercial apparatuses and set-ups for determining and measuring the fluorescence of a sample, which include fluorescence spectroscopy, fluorescence microscopy, and confocal laser scanning microscopy. Such methods are readily available or easily researchable in available publications.

One method for measuring fluorescence in samples is through the use of fluorimeters. Radiation is passed through the sample under controlled conditions (e.g. constant temperature and pressure). As the radiation passes through the sample at an excitation wavelength, the fluorescence sensor in the sample emits distinct spectral properties (such as emission spectra), which then are captured as data by the optics of the fluorimeter. Both excitation and emission spectra are taken to determine the excitation and emission maxima for optimal fluorescence signals and parameters, which depend on the microenvironments. Optimal fluorescence signal may be obtained at any excitation and emission wavelengths near respective corresponding maxima. The data is saved on a computer and or it can be further analyzed by the computer. The scanned data then is compared to control samples, i.e. calibration samples, so to determine the concentration of the analyte in the sample. Specifically, the analyte concentration may be determined by extrapolating the fluorescence of the sample with a calibration curve. This assay may be applied to purified fluorescent proteins or any cell mixture with expressed fluorescent proteins.

Targeting the Fluorescent Sensor

The analyte binding protein, e.g. the fluorescent protein, may include a nucleotide targeting sequence that directs the fluorescent protein to particular cellular sites. By fusing the appropriate organelle targeting signal proteins or localized host proteins to the fluorescent proteins, the fluorescent protein may be selectively localized in cells. Such a targeting sequence, which may code for organelle targeting signal or host proteins, may be ligated to the 5' terminus of a nucleotide, thus encoding the fluorescent protein such that the targeting peptide is located at the amino terminal end of the fluorescent protein.

Such signal proteins are known to those with ordinary skill in the art and may be readily obtained without undue experimentation or research. For example, the fluorescent protein may be directed to and transported across the endoplasmic reticulum by fusing the appropriate signal protein. Once secreted, the protein then is transported through the Golgi apparatus, into secretory vesicles, and into the extracellular space, preferably, the external environment. Signal peptides or proteins that may be used with this invention include prepro peptides that contain a proteolytic enzyme recognition site.

As disclosed, the fluorescent sensor is particularly useful in detecting and quantifying $Ca^{2+}$ or the flux thereof in a microenvironment of the endoplasmic reticulum. The fluorescent sensor may be expressed and targeted to specific cellular organelles, e.g. the endoplasmic reticulum, for selectively monitoring the $Ca^{2+}$ concentration therein. As the fluorescent sensors may be comprised of an amino acid sequence that targets the fluorescent sensor to a specific cell or intracellular location, the fluorescent sensor functions as a reporter and generates an optically detectable signal.

The localization sequence may be a nuclear localization sequence, an endoplasmic reticulum localization sequence, a peroxisome localization sequence, a mitochondrial localization sequence, or a localized protein. Localization sequences may be targeting sequences that are described, for example, in Stryer, L., Biochemistry, Chapter 35—Protein Targeting (4th ed., W. H. Freeman, 1995). Some known localization sequences include those targeting the nucleus (KKKRK), (SEQ ID NO: 5), mitochondrion (amino terminal MLRTSS-LFTRRVQPSLFRNILRLQST–), (SEQ ID NO: 6) endoplasmic reticulum (KDEL (SEQ ID NO: 7) at C-terminus, assuming a signal sequence present at N-terminus, e.g. MLLSVPLLGLLGLAAD (SEQ ID NO: 8)), peroxisome (SKF at the C-terminus), synapses (S/TDV or fusion to GAP 43, kinesin and tau), prenylation or insertion into plasma membrane (CAAX, CC, CXC, or CCXX at C-terminus), cytoplasmic side of plasma membrane (chimeric to SNAP-25), or the Golgi apparatus (chimeric to furin). One of ordinary skill in the art can determine localization sequences suitable to the present invention without undue research and experimentation.

Production and Expression of the Fluorescent Sensor

The analyte sensor may be produced as chimeric proteins by recombinant DNA technology. Recombinant production of proteins including fluorescent proteins involves expressing nucleic acids having sequences that encode the proteins. Nucleic acids encoding fluorescent proteins can be obtained by methods known in the art. For example, a nucleic acid encoding the protein can be isolated by a polymerase chain reaction of DNA from *A. victoria* using primers based on the DNA sequence of *A. victoria* GFP. Mutant versions of fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

In the chimeric proteins of the invention, the sensor polypeptide is inserted into an optically active polypeptide, which responds (e.g., a conformation change) to, for example, a cell signaling event. Cell signaling events that occur in vivo can be of a very short duration. The optically active polypeptides of the invention allow measurement of the optical parameter, such as fluorescence, which is altered in response to the cell signal, over the same time period that the event actually occurs. Alternatively, the response can be measured after the event occurs (over a longer time period) as the response that occurs in an optically active polypeptide can be of a longer duration than the cell signaling event itself.

In the present invention, the nucleic acid sequences encoding the fluorescent sensor may be inserted into a recombinant vector, which may be plasmids, viruses or any other vehicle known in the art, that has been manipulated by the insertion or incorporation of the nucleic acid sequences encoding the chimeric peptides of the invention. The recombinant vector typically contains an origin of replication, a promoter, as well as specific genes that allow phenotypic selection of the transformed cells. Vectors suitable for use in the present invention include but are not limited to the T7-based expression vector for expression in bacteria or viral vectors for expression in mammalian cells, baculovirus-derived vectors for expression in insect cells, and cauliflower mosaic virus (CaMV), tobacco mosaic virus (TMV), and other vectors.

Depending on the vector utilized, any of a number of suitable transcription and translation elements, including constitutive and inducible promoters, transcription enhancer elements, transcription terminators, etc., may be used in the expression vector. Such construction of expression vectors and the expression of genes in transfected cells can involve the use of molecular cloning techniques (e.g. in vitro recombinant DNA techniques, synthetic techniques and in vivo recombination/genetic recombination), bacterial system for the expression of vectors, yeast systems with constitutive or inducible promoters, insect systems, prokaryotic and eukaryotic systems using transfection or co-transfections of DNA vectors, transgenic animals using for example viral infection, and embryonal stem cells. Methods and procedures for using and applying such vectors are widespread in publications and are known or easily obtainable by persons of ordinary skill in the art.

EXAMPLES

1. Fluorescent Proteins with $Ca^{2+}$ Binding Sites

Exemplary fluorescent proteins having GFP chromophore and grafted $Ca^{2+}$ binding motifs may be constructed, expressed, and targeted to the ER of mammalian cells. More particularly, as shown in FIG. 1, the 3-dimensional structure of an exemplary GFP is designed with $Ca^{2+}$ binding motifs at specific binding sites, which are the chromophore-sensitive locations. Particularly, sites suitable for the introduction of $Ca^{2+}$ binding motifs include the amino acid residues between 156-157 and 172-173 of the GFP.

Figure 2A:
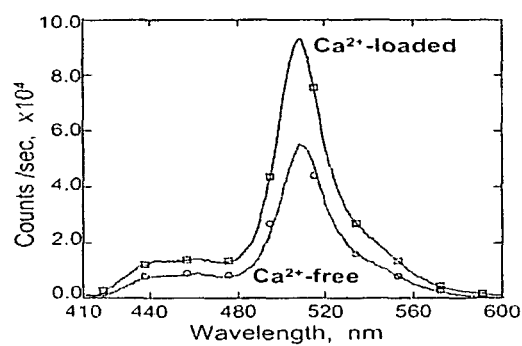
FIGS. 2A-B illustrate the fluorescence properties of Sensor-G1 excited at 398 nm.
Figure 2B:
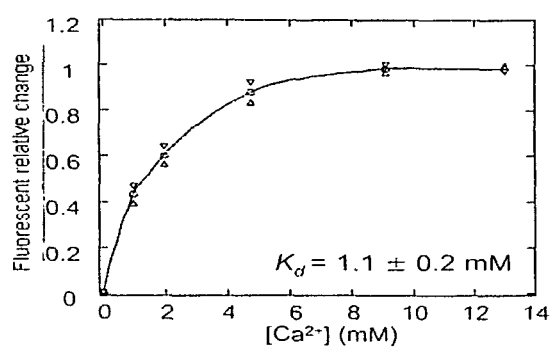

FIG. 2 shows data from an exemplary GFP analyte sensor that binds $Ca^{2+}$ developed with the grafting approach. In the absence of $Ca^{2+}$, this sensor has one major emission maximum at 510 nm. As the addition of $Ca^{2+}$ resulted in a 500% increase of its emission at 510 nm, the fluorescence enhancement is $Ca^{2+}$ specific. The analyte sensor displayed a $Ca^{2+}$ dependant fluorescent protein in the $Ca^{2+}$ concentration ranged from 0.0 mM to 1.150 mM. Further, the analyte sensor had $K_d$=1.1±0.02 mM.

Figure 3:
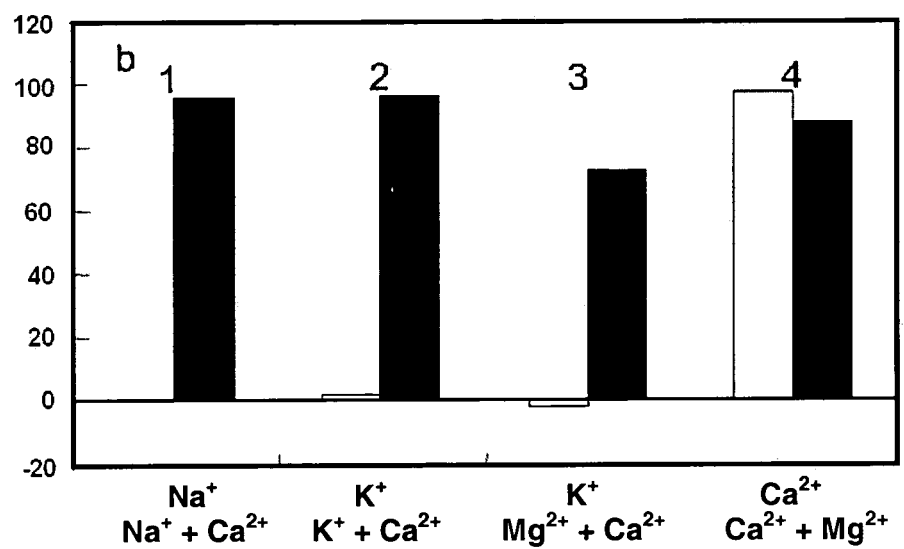
FIG. 3 illustrates that the analyte sensor tailed for $Ca^{2+}$ is selective for $Ca^{2+}$ over other analytes $Na^+$, $K^+$ and $Mg^{2+}$.

FIG. 3 shows that the fluorescent sensor is relatively noncompetitive with other ions such as $Na^+$, $Mg^{2+}$ or $K^+$. The relative fluorescence emitted by the sensor at 464 nm in the presence of competing ions was compared to its signal without competing ions. More particularly, lane 1 compares the fluorescence from the sensor in 95 mM $Na^+$ with 95 mM $Na^{2+}$ and $Ca^{2+}$, lane 2 compares the fluorescence from the sensor in 95 mM $K^+$ with 95 mM $K^+$ and $Ca^{2+}$, lane 3 compares the fluorescence from the sensor in 9.5 mM $Mg^{2+}$ with 9.5 mM $Mg^{2+}$ and $Ca^{2+}$, and lane 4 compares 0.83 mM $Ca^{2+}$ with 0.83 mM $Ca^{2+}$ and $Mg^{2+}$. As can be seen, the sensor is most responsive to $Ca^{2+}$ and less dependant on the presence of other ions. The addition of 9.5 mM $Mg^{2+}$ does not significantly reduce the signal, which indicates that $Mg^{2+}$ does not substantially compete with $Ca^{2+}$ in the binding motif of the sensor.

2. Designing a $Ca^{2+}$ Binding Motif using the Grafting Method

A $Ca^{2+}$ binding motif may be constructed using a grafting method from the EF-hand motif, which is $Ca^{2+}$ binding site highly conserved throughout nature (more than 5000 proteins contain this motif). This motif consists of an EF-hand calcium-binding loop and flanking two helices (helix-linker-loop-linker-helix). By selectively manipulating the primary, secondary, tertiary, and/or quaternary structure of the EF-hand motif for optimal connection of the calcium binding motif without globally altering the structure of the fluorescent protein, it is possible to control the affinity and selectivity of the $Ca^{2+}$ binding motif.

Specifically, $Ca^{2+}$ binding motifs with different $Ca^{2+}$ binding affinities may be created using a grafting method. The grafting method involves varying residues in calcium binding loops, helices, and linkers to obtain various $Ca^{2+}$ binding affinities with dissociation values ranging from 10 uM to 5.0 mM. Furthermore, $Ca^{2+}$ sensors with stronger affinities to and better selectivity for $Ca^{2+}$ over other ions such as $Mg^{2+}$ may be achieved by designing different ligand types and changing the number of charged ligand residues to form $Ca^{2+}$ binding pockets.

The $Ca^{2+}$ binding affinity of the calcium binding motif may be varied by changing the charged side chains that are present on the calcium-binding loop and the neighboring environment. As $Ca^{2+}$ ligand residues directly contribute to the binding affinity of $Ca^{2+}$, the replacement, for example, of the residues at loop positions 1 (Asp) and 12 (Glu) of the EF-hand motif by Ala and other amino acids dramatically reduces calcium binding affinity up to 100 times. See Linse, S. and Forsen, S., Adv. Second Messenger Phosphoprotein Res. 30, 89-151 (1995).

Further, the $Ca^{2+}$ binding affinity of a $Ca^{2+}$ bind motif comprising the EF-hand motif may be varied by modifying the flanking helices. The residues on the flanking helices can be modified by changing their properties, such as hydrophobicity, helical propensity and charge interactions with different amino acids. These changes can be made so as to tune calcium binding affinity and fluorescence signal strength and spectra. A variation in the $Ca^{2+}$ binding site results from having no EF-loop helices, a single flanking E or F helix, or both EF-helices. Attaching the flanking F helix results in an increase in $Ca^{2+}$ affinity approximately 10 times. Modifying flanking helices with different affinities to analyte and conformational properties can result in different perturbations of the chromophore environment, which in turn produces different optical signals for detection.

As the charged side chains exhibit a strong influence on the metal (analyte) binding affinity even though they are not directly involved as ligands, variation of these chains results in variations in metal (analyte) binding affinities and selectivity. For example, the removal of three negatively charged residues, glutamate, aspartate and glutamate, at positions 17, 19, and 26 in the vicinity of the EF-hand calcium binding sties and on the surface of calbindin$_{d9k}$ may result in up to a 45-fold decrease in the average affinity (per site). See Linse et al., Nature, 335 (6191): 651-2 (Oct. 13, 1988). Further, the replacement of polar side chains at glutamine and lysine at (positions 41 and 75) outside the EF-loop with non-polar side chain leads to dramatic decreases in the $Ca^{2+}$-binding affinity of N-terminal domains of calmodulin. See Linse, S. and Forsen, S., Adv. Second Messenger Phosphoprotein Res. 30, 89-151 (1995). Stabilization of the helices by increasing charge interaction of the side chains will enhance calcium affinity by stabilizing required calcium binding coordination chemistry.

The $Ca^{2+}$ binding affinity and selectivity may be changed by varying the linkers that are used to connect the calcium binding motif to the fluorescent protein. For example, the grafted EF-loops containing zero, one, or two glycine linkers each exhibit distinct calcium binding affinities. Using such EF-loops, it was shown that the $Ca^{2+}$ binding affinity of an EF loop-I of calmodulin with two glycine linkers has a $K_d$ for calcium of 0.01 mM but exhibits a $K_d$ of 0.18 mM when it was without the glycine linker. See Ye, Y. M., Lee, H. W., Yang, W., Shealy, S. J., Liu, Z. R., and Yang J. J., Protein Eng. 14, 1001-1003 (2001). Preferably, the length of the linkers is between 0 and 10 residues, e.g. 0 to 10 glycine residues or different combinations of residues. Where a linker moiety is present, the length of the linker moiety is chosen to optimize the kinetics and specificity of responsiveness of the fluorescence sensor.

As such, one of ordinary skill in the art may vary the EF-hand motif by varying the primary, secondary, tertiary, and/or quaternary structure of the $Ca^{2+}$ binding site.

3. Designing a $Ca^{2+}$ Binding Site using the Computation Design Approach.

In this example, the computation design approach is executed by an algorithm that can locate potential calcium binding sites in proteins or molecules based on the geometric description of the $Ca^{2+}$ binding pockets. In these pockets, $Ca^{2+}$ is predominantly chelated with oxygen from several types of groups such as carboxylates (bi- and mono-dentate interactions) of aspartates, glutamates, carbonyls (main-chain any amino acids (Gly preferred) or amide side-chain of asparagines and glutamines), and hydroxyls either from protein side-chains of serine, thronine or solvent hydroxyls such as water. Oxygen atoms from these molecules commonly form pentagonal bipyramidal or distorted octahedral geometries. This pocket usually has a coordination number from 6 to 9 with one to three coordinating ligands contributed by solvent molecule.

More particularly, a $Ca^{2+}$-binding protein design was carried out on an SGI O2 computer using the Dezymer program following the procedure established in Yang, W., Lee, H., Hellinga, H. and Yang, J. J., Proteins 47, 344-356 (2002). A geometric description of the ligands around the metal, the three-dimensional structure of the backbone of a protein, and a library of a side-chain rotamers of amino acids were input into the Dezymer algorithm to identify the set of potential metal binding sites. The first residue located in the calculation (called anchor) defines the relative position of the calcium atom to the protein backbone and is used as a starting point to construct a $Ca^{2+}$-binding site. After attaching the anchor residue to the backbone of the protein along the protein sequence, the calcium-binding geometry or positions of other ligands are then defined around the anchor.

Figure 4:
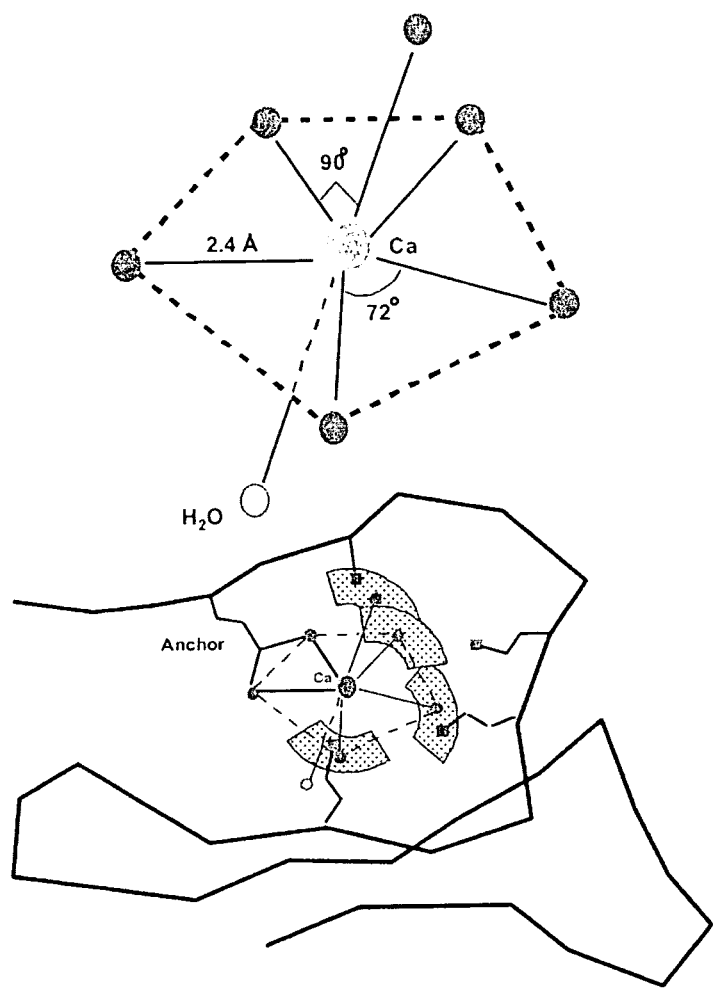
FIG. 4 is model of a $Ca^{2+}$ binding site based on the geometric properties.

Specifically, after attaching the anchor residue to the backbone of the protein along the protein sequence, the $Ca^{2+}$-binding geometry or positions of other ligands are then defined around the first molecule. As shown in FIG. 4, the parameters derived from the ideal pentagonal bipyramidal geometry with allowed floating ranges for Ca—O lengths (2.0-3.0 Å, ideal is 2.4 Å), O—Ca—O angles (30-120°, 90-180°, and 45-135° for the ideal values of 72°, 144° and 99°, respectively), and C—O—Ca—O dihedral angles (0-45° for those on the plane and 45-135° for those off the plane) were used in the first step of the finding step. The constructed sites were minimized based on the ideal geometry in the second step of optimization.

Thus, the $Ca^{2+}$ binding site in the fluorescent protein may be designed with a pentagonal bipyramidal geometry with seven ligands using computational algorithms. One bidentate glutamate and four unidentate ligands selected from glutamate, aspartate, asparagines, and/or glutaminae were used for the calculations. The parameters derived from the ideal pentagonal bipyramidal geometry with the floating ranges for Ca—O lengths, O—Ca—O angles, and C—O—Ca—O dihedral angles disclosed above were used in the first step.

As shown in Table 1, 50% of the designed $Ca^{2+}$ binding sites are located in the loop sites clustered at beta-strands near the chromophore, which may be a water cavity in the architecture of the protein. The $Ca^{2+}$ binding sites are able to selectively binding calcium over $Tb^{3+}$ or vice versa. About 10000 potential $Ca^{2+}$ binding sites have been produced using such algorithms.

TABLE 1

Metal Binding Affinity of The $Ca^{2+}$ sensor

| No. | Site | Kd (μM) $Ca^{2+}$ | Kd (μM) $Tb^{3+}$ | Extinction Coefficient $\times 10^3 M^{-1} cm^{-1}$ | Fluorescence Quantum Yield At $\lambda$ em |
|---|---|---|---|---|---|
| 1 | Sensor-G0 | | 2.56 ± 0.29 | | |
| 2 | Sensor-G0b | | 2.41 ± 0.10 | | |
| 3 | Sensor-G2 | 46.3 ± 3.4 | | $\epsilon_{490} = 62$ | $\phi_{574} = 0.60$ |
| 4 | Sensor-G2n | n/a | n/a | $\epsilon_{490} = 61$ | $\phi_{574} = 0.63$ |
| 5 | Sensor-G1 | 1070 ± 2 | | $\epsilon_{490} = 54$ | $\phi_{574} = 0.48$ |
| 5 | Sensor-G1n | n/a | n/a | $\epsilon_{490} = 57$ | $\phi_{574} = 0.54$ |
| 6 | Sensor-G1c | 82.1 ± 5.7 | | | |
| 7 | EGFP (reference) | | | $\epsilon_{490} = 55$ | $\phi_{507} = 0.60$ |

As shown in Table 1, the GFP variants (Nos. 3, 5, and 6) with a single designed $Ca^{2+}$ binding site have high expression yields, have been purified in large quantities, and have strong $Ca^{2+}$ affinity and selectivity. As shown in Table 1, N and C (Nos. 4, 5, and 6) are the sensor variants with Gly linker at the N and C terminal of the metal (analyte) binding motif, respectively. As 150 mM KCl and 10 mM $Mg^{2+}$ are not able to compete for the sites, it was likely that the sites are highly specific to the tailored ion.

4. The Sensitivity of $Ca^{2+}$ Sensor ranged from 10 μM-1.0 mM

The $Ca^{2+}$ binding sensitivity was examined by introducing a tailored $Ca^{2+}$ binding motif into GFPs and measuring the dissociation constants. The $Ca^{2+}$ binding constant of the developed EGFP variants have been obtained by monitoring their fluorescence change at 510 nm as a function of metal concentration with an excitation wavelength at 398. Table 1 lists the fluorescence signal change at 510 nm can be fitted with an equation assuming the formation of a metal-protein complex of 1:1 with a dissociation constant ($K_d$) of 1.0 mM. This result was similar to the results obtained by the competition of Mag-Fura-2. As shown in Table 1, the measured $K_d$ of $Ca^{2+}$ for several GFP sensors with $K_d$ values ranging from 20 uM-1.0 mM. As shown in FIG. 2, the fluorescence of fluorescence sensor (in 10 mM MES and 1 mM DTT) changes with the different $Ca^{2+}$ concentrations. In each case, the sample was excited with radiation of 398 nm and the fluorescence was measured across the 400-600 nm band. These results show that the fluorescent sensor may be use used as a $Ca^{2+}$ sensor.

5. $Ca^{2+}$ Sensors are Expressed In Vivo.

The fluorescent sensor comprising mutant GFP and a grafted $Ca^{2+}$ binding motif in HeLa and Vero cells showed the that fluorescent sensor was expressed so that cells maintained their integrity in vivo. These stable cell lines were grown in medium supplemented with antibiotic selection (0.2 mg/ml Geneticin). Specifically, GFP variants (GFP Sensors G1 and G2) and a GFP-fused to the coat protein of Rubella virus were subcloned into pcDNA3 (a vector for the expression of proteins in mammalian cell lines). After verification by DNA sequencing, the vector was transiently transfected into HeLa and Vero cells using the established protocol. See Pugachev K. V., Tzeng W. P., Frey T. K., Signaling Pathways between the Plasma Membrane and Endoplasmic Reticulum Calcium Stores, Cell Mol Life Sci, 57, 1272-86 (2000). An Axiovision upright microscope at 40× magnification with exposure times of 500 and 1500 ms was used to examine the fluorescent protein in HeLa and Vero cells. This examination showed that the transfected cells illuminated a fluorescence pattern in vivo.

Figure 5:
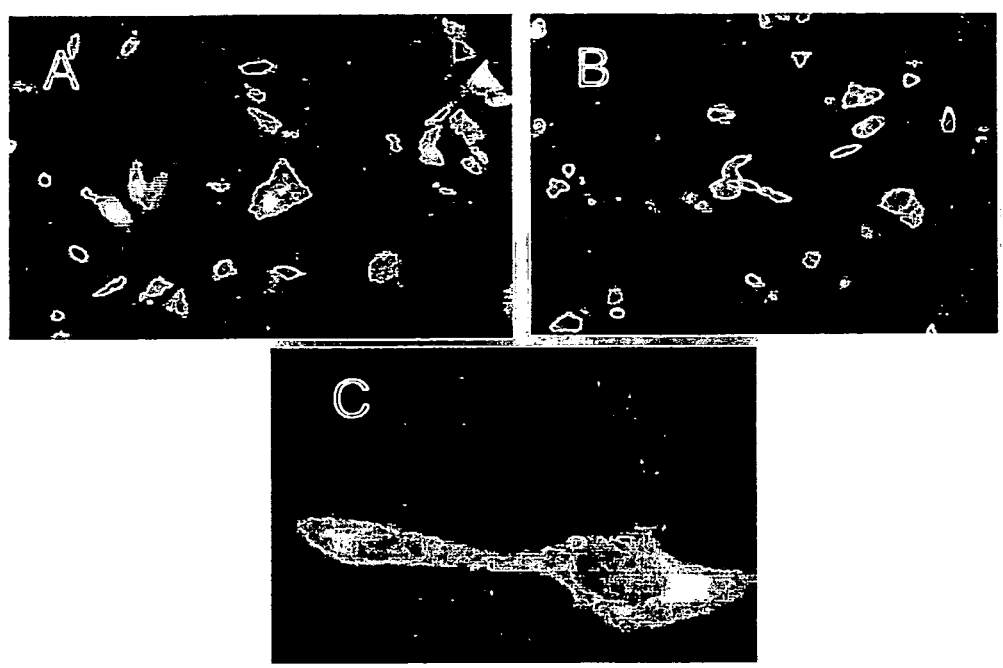
FIGS. 5A-C illustrate three exemplary GFP variants with the grafted $Ca^{2+}$ binding motif.
Figure 6:
FIG. 6 illustrates Sensor-G2 in mammalian HeLa cell lines.

As shown in FIGS. 5 and 6, all GFP variants with grafted $Ca^{2+}$ binding motif are expressed in mammalian cell lines with strong green fluorescence that appears largely cytosolic. Further, the GFP variant fused with the ER-Tag of capsid protein of Rubella virus was specifically expressed in the ER. See Zheng D. P., Zhu H., Revello M. G., Gerna G., Frey T. K., Phylogenetic analysis of Rubella virus Isolated during a period of epidemic transmission in Italy, 1991-1997, J. Infect. Dis, 187, 1587-97 (2003). These results show that the GFP $Ca^{2+}$ sensors maintain their fluorescent properties in vivo and that GFP can be directed into cells in vivo. Further, the results show that the fluorescent sensor when introduced into the cells, which were grown for several weeks, is not toxic to such cells.

Figure 7:
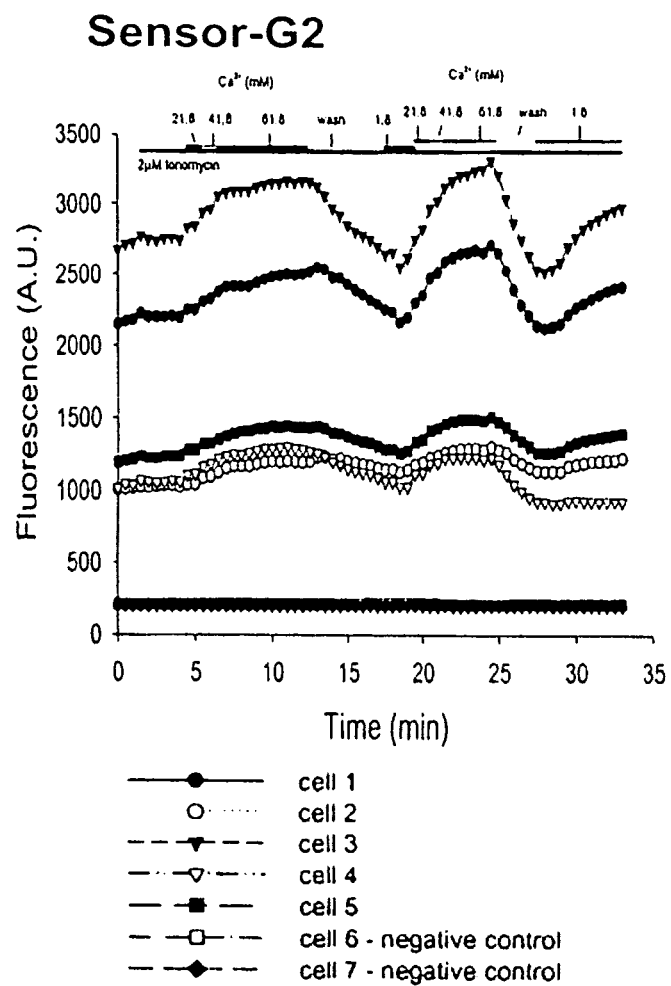
FIG. 7 illustrates the free calcium dynamics in the cytosol of HeLa cells visualized with Sensor-G2. The calcium channel is opened with the addition of ionomycin and the fluorescent intensity of the sensor is increased because of the addition of calcium (1.8 to 61.8 mM). The decrease of fluorescent intensities is also observed by washing the HeLa cells with buffer solution.

6. Fluorescence Indicates $Ca^{2+}$ Concentration $Ca^{2+}$ binding sites in proteins created by grafting continuous $Ca^{2+}$ binding motifs into host fluorescent proteins are $Ca^{2+}$ concentration sensors. An example fluorescent protein, labeled Sensor-G1 in Table 1, includes an isolated EF-loop III from Calmodulin with both glycine linkers attached to both ends of the protein. As shown in FIGS. 2 and 7, the fluorescent properties of the fluorescent protein vary when 5 mM $Ca^{2+}$ is added to the in vitro sample. Further, a titration of the fluorescent protein shows that the relative fluorescence changes as the $Ca^{2+}$ increases from 0 to greater than 13 mM. Thus, fluorescence or relative fluorescence is a sensor of the $Ca^{2+}$ sample.

FIG. 7 shows the responsiveness of the analyte sensor in HeLa cells in the presence of the channel opening drug ionomycin. The free $Ca^{2+}$ dynamics in the cytosol of HeLa cells is detected by the analyte sensor. The responsiveness of the analyte sensor is consistent with the pathway of the drug. More particularly, as the $Ca^{2+}$ channels were opened by the addition of ionomycin, the fluorescent intensity of the sensor increased reflecting the addition of $Ca^{2+}$ in the cell. Further, after the cells are washed, the fluorescent intensity of the sensor decreased reflecting the decrease in $Ca^{2+}$ in the cell.

7. Calibration of an Analyte Sensor

The accurate calibration of an exemplary $Ca^{2+}$ sensor is optimal for reliable ion measurements. The calibration may be accomplished using the common $Ca^{2+}$ indicator Fura-2 in which the zero and maximum fura-2 fluorescence, using 224 nM free $Ca^{2+}$ as the dissociation constant of fura-2 for $Ca^{2+}$, are used to calculate a calibration curve. See Grynkiewicz G., Poenie, M., Tsien R. Y., A New Generation of Calcium Indicators with Greatly Improved Fluorescence Properties, J. Biol. Chem., 260, 3440-3450 (1985). Such a calibration may be confirmed also by a 11-point Fura-2 calibration kit supplied by Molecular Probes.

Each grafted $Ca^{2+}$ sensor is calibrated for changes in fluorescence as a function of $[Ca^{2+}]$. Although these sensors ultimately will be expressed in the ER, purified protein is used initially to design $Ca^{2+}$ calibration curves. Subsequent calibration curves may be conducted with the use of saponin permeabilized HeLa or primary lens cells using both epifluorescence and laser scanning confocal microcopy, and subsequently using a DeltaVision multi-wavelength deconvolution microscope.

These initial calibration curves may measure the in vitro and in situ dynamic ranges of $Ca^{2+}$ induced fluorescence changes. In vitro calibration may be conducted by using buffers containing a designed $Ca^{2+}$ sensor and a known $Ca^{2+}$ concentration (using $Ca^{2+}$ chelators such as EGTA and EDTA), applying these solutions between glass coverslips and slides, measuring the fluorescence of each solution, and constructing a standard curve. In order to mimic the cytoplasmic and ER ion environments, standard curves may be constructed from two buffers with a 10-fold difference in ion strength. If the $Ca^{2+}$ sensors are pH sensitive, standard curves may be constructed for three pH values spanning the physiologically relevant range (pH 6.8-7.4). Microspheres may be added to each solution to maintain a constant thickness between the glass coverslips and slides.

Well-characterized cell permeable $Ca^{2+}$ sensor dyes with dissociation constants for $Ca^{2+}$ ranging from the submicromolar to the hundreds of micromolar (e.g. Fura-2 AM, Kd=140 nM; Fluo-5F Am, Fluo-4ffA<.Ld=9.7 uM; furaptra, Kd=54 uM; Fluo-5n AM, Kd=90 uM; X-Rhod-5N Am, Kd=350 um) may be used to demonstrate that changes in the designed $Ca^{2+}$ sensors to an intracellular environment. Calibration of the $Ca^{2+}$ sensor localized to the ER may be accomplished in situ as described by Golovina and Blaustein. See Golovina V. A., Blaustein M. P., Spatially and Functionally Distinct Calcium Stores in Sacroplasim and Endoplasmic Reticulum, Science, 275, 1643-8 (1997). More particularly, the calibration of the $Ca^{2+}$ sensors may be accomplished using the following equations for either a single wavelength or ratiometrically:

$$[Ca^{2+}] = K_d (F - F_{min})/(F_{max} - F), \text{ where F is the emitted fluorescence} \quad (1)$$

$$[Ca^{2+}] = K_d \{(R - R_{min})(F_{min})\}/\{(R_{max} - R)(F_{max})\} \quad (2)$$

The cells are super fused with $Ca^{2+}$-free "intracellular solution" containing 1 mM EGTA. Saponin (30 mg/ml) then is added to a permeabilized solution containing inhibitors of ATP production to thus inhibit $Ca^{2+}$ pumps. $F_{min}$ and $R_{min}$ then are determined by addition ionophores to the $Ca^{2+}$-free calibration solution to equilibrate the extra- and intraorganellar $[Ca^{2+}]$. $F_{max}$ and $R_{max}$ then are measured by adding 10 mM $Ca^{2+}$. Thereafter, the measurements may be corroborated by comparison with GFP-CaM cameleon proteins both in vitro and in situ.

8. Targeting of Fluorescent Proteins

A fluorescent protein with an engineered $Ca^{2+}$ binding site may be targeted to the ER. The fluorescent protein CRsig-GFP-KDEL comprises, cGFP, KDEL (SEQ ID NO: 7) (an ER retention signal) at the C-terminal, and the sequence MLLS-VPLLLGLLGLAAAD (SEQ ID NO: 9) (CRsig) at the N-terminal of GFP-KDEL. The CRsig signal peptide of the protein is thought to direct the fluorescent peptide of the protein, i.e. the GFP, to the ER. Optionally, the Kozak consensus sequence (kz), STM, may be added to the N-terminal of CRsig-GFP-KDEL (denoted as kz-CRsig-GFP-KDEL) for optimal translational initiation in mammalian cells. Ordinary cGFP without special targeting signals is expected to distribute in the cytosolic compartment, as shown in FIGS. 5 and 6.

9. Metal-Binding Protein with Desired Structure and Cell Adhesion Function

Figure 8:
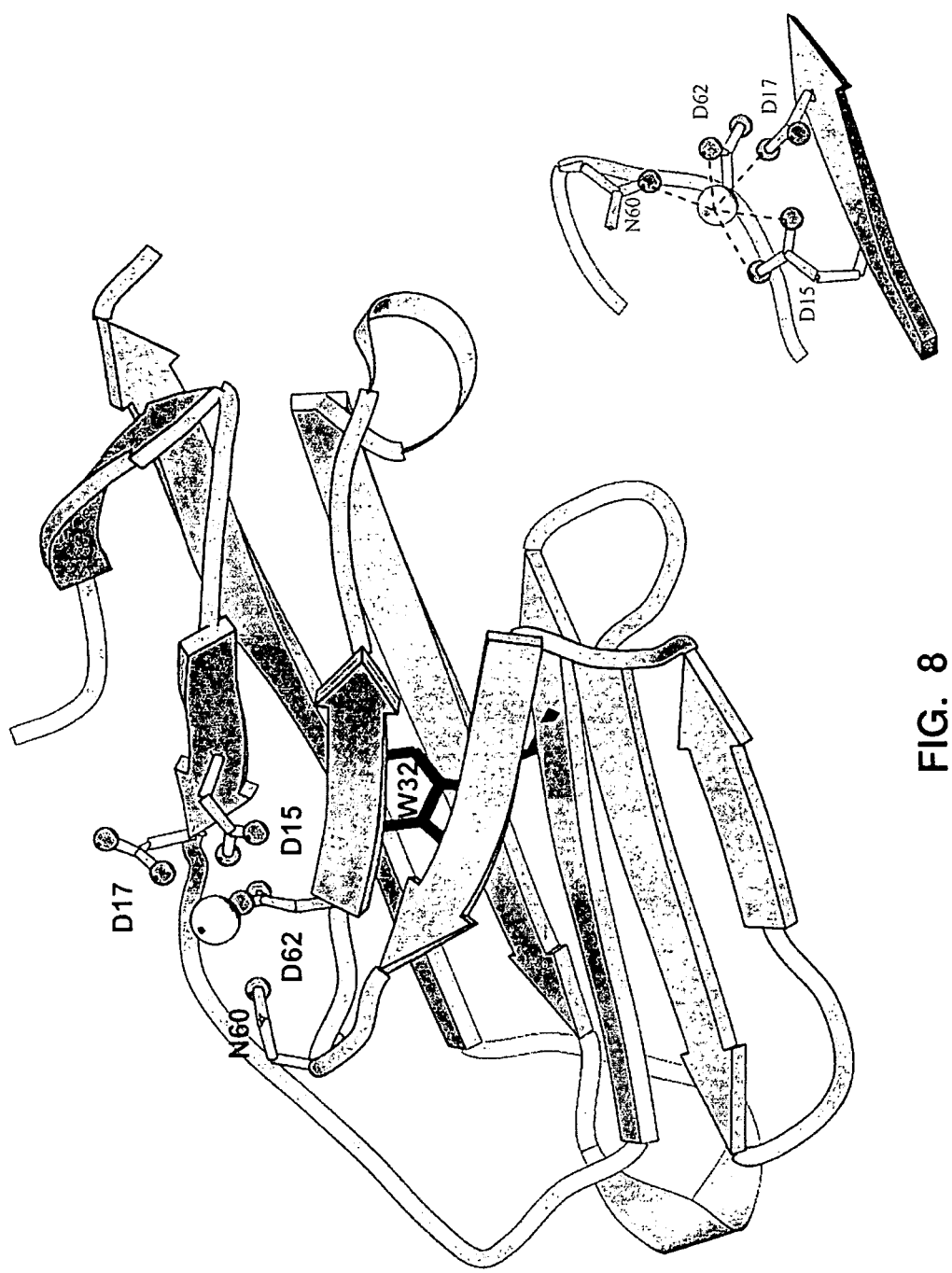
FIG. 8 illustrates the structure of a CD2 protein (Ca.CD2) tailored into a specific receptor for $Ca^{2+}$ using the computational design approach.

A computational design approach may used to construct metal (analyte) binding sites into non-binding metal (analyte) proteins. More particularly, in one example, a computational design approach was used to construct a single $Ca^{2+}$ binding motif in a non-$Ca^{2+}$-binding protein. A rationally designed stable $Ca^{2+}$ binding motif was operatively linked with a natural host protein CD2 (one of the most extensively studied non-calcium binding cell adhesion proteins with a common structure topology of the Ig-fold in over 3000 proteins) so to preserve the biological function of the host protein and the nature of the binding folding of the binding site. As shown in FIG. 8, CD2 was converted into a specific receptor for $Ca^{2+}$ (Ca.CD2). The binding sites may be designed and engineered into a functional protein without a global conformational change in two stages.

At the first stage, preliminary $Ca^{2+}$ binding sites were developed using the pentagonal bipyramidal geometry to describe the structural parameters of the calcium binding sites, which are available in literature databases. More particularly, one bidentate Asp and three unidentate ligands from Asp, Asn, Glu, Gln, Thr, and or Ser were used for the calculations and development of the preliminary binding sites. To reduce steric crowding of the site, two positions in the primary coordination of pentagonal bipyramidal geometry were unoccupied as many calcium-binding proteins have 1-3 oxygen ligand atoms from solvent water. Also, these sites were then minimized based on the target geometry.

Figure 9:
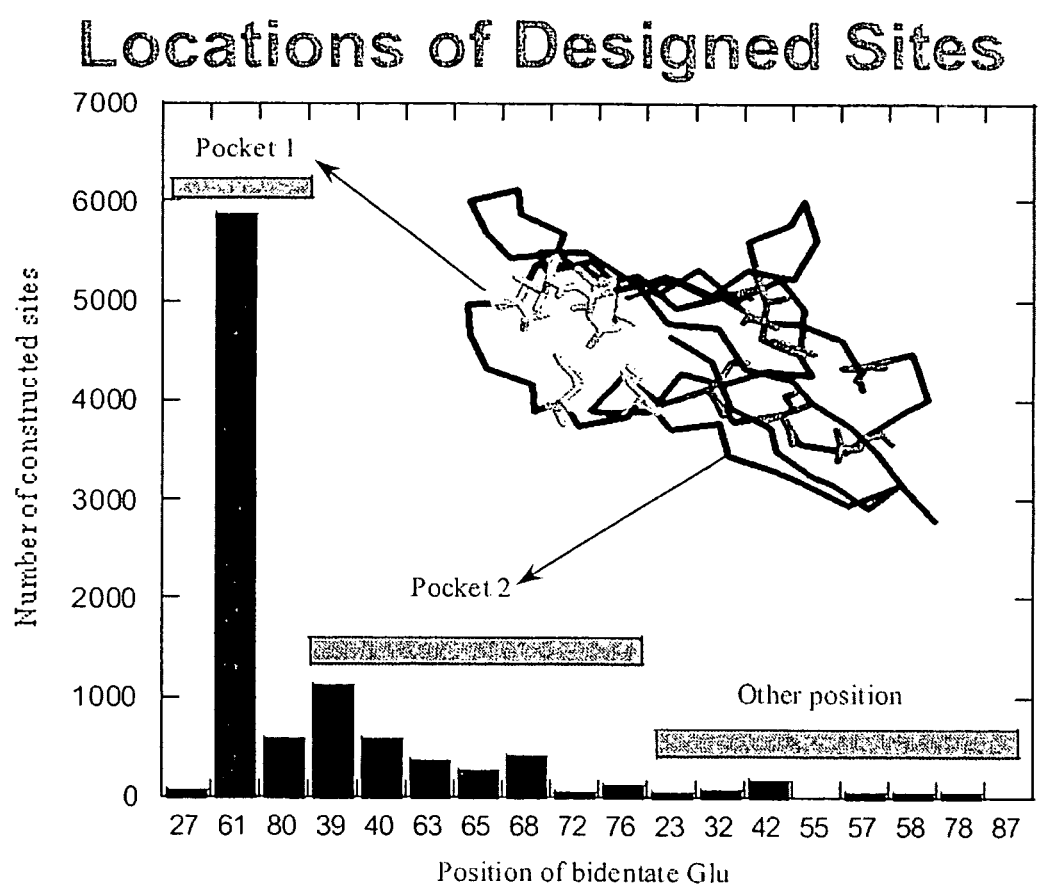
FIG. 9 illustrates about 10,000 different potential calcium-binding sites generated through the computational design approach.
Figure 10:
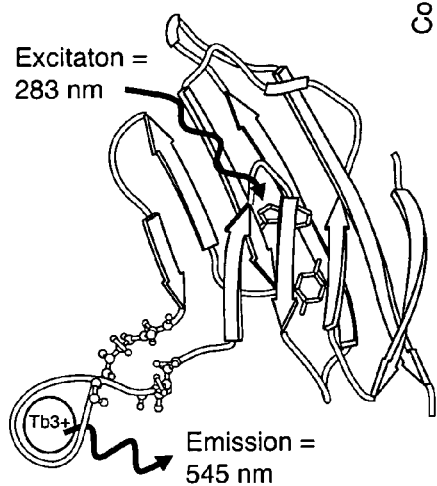
FIG. 10 illustrates an exemplary analysis of an analyte sensor using $Tb^{3+}$ fluorescence.
Figure 10:
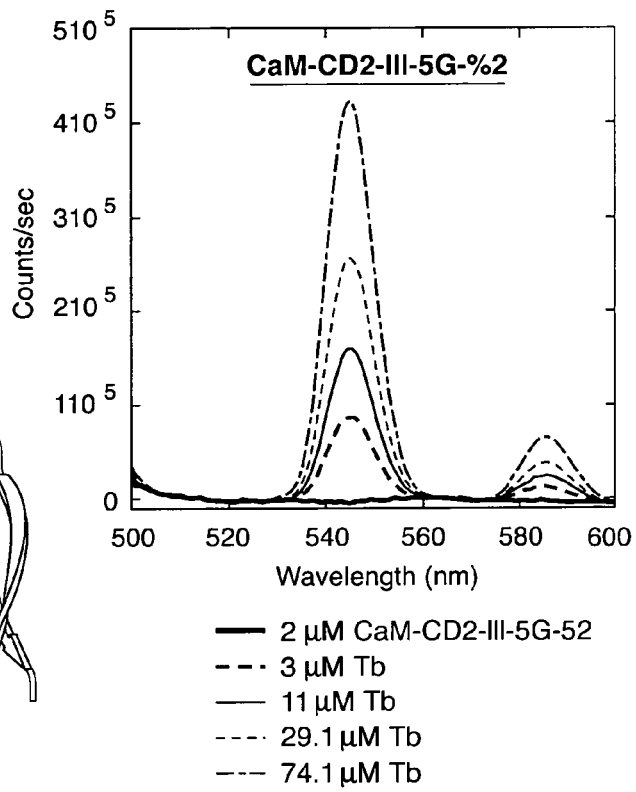
Figure 10:
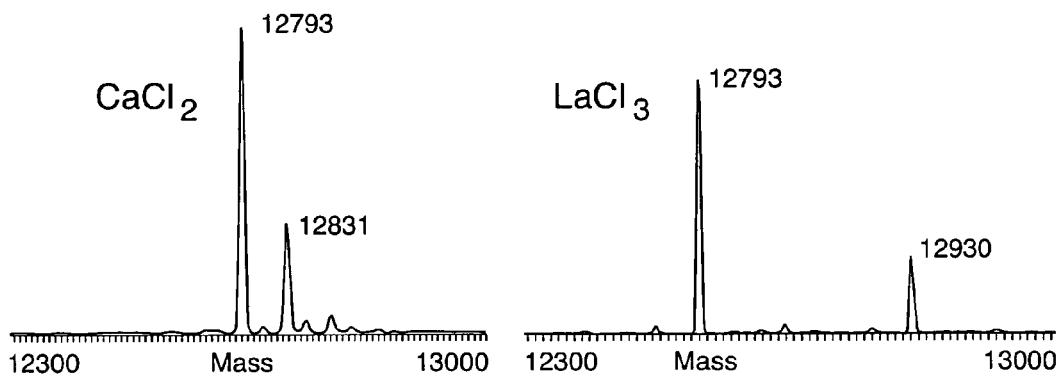
Figure 11:
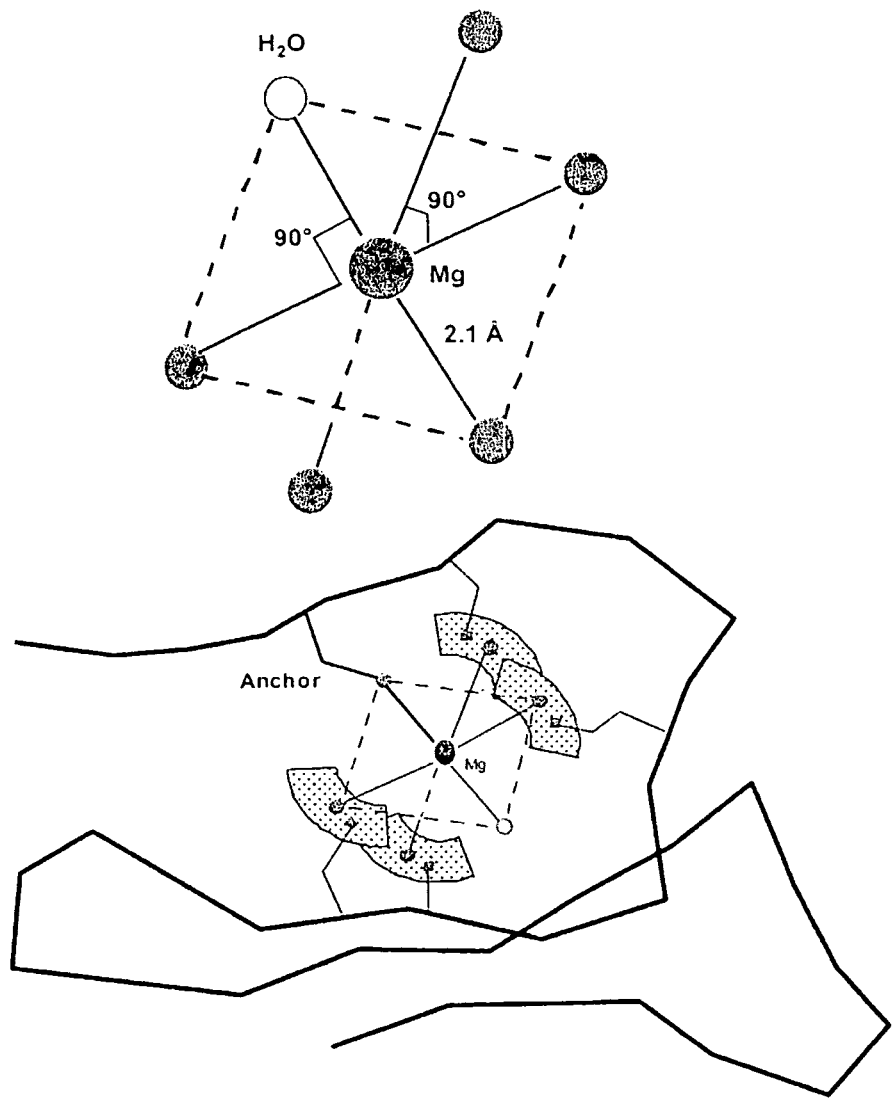
FIG. 11 is model of a $Mg^{2+}$ binding site based on the geometric properties.

As shown in FIG. 9, about 10,000 different potential calcium-binding sites with the popular pentagonal geometry can be constructed in CD2-D1. The sites are mainly located at the pocket (pocket 1) enveloped by BC loop with C, F, G β-strands and FG loop or the pocket (pocket 2) enveloped by CC' loop and C', E, F β-strands. More than half of the sites are located at pocket 1. Of these, positions 18, 21, 27, 30, 80, 88, and 89 are mostly used as ligands with different combinations and the position 61 is the most frequently used for the bidentate ligand Glu. In pocket 2, positions 39, 63, 65, 68, 72, and 76 are all frequently used for bidentate and unidentate ligands.

At the second stage, algorithms were used to rationally evaluate the generated preliminary $Ca^{2+}$ binding sites. More particularly, algorithms were used to evaluate the nature of the binding sites according to the number of charged ligand residues, the number of mutated ligand residues, the accessibility of solvent, and the alterations of hydrogen bonding and hydrophobic packing. The designed calcium-binding sites in CD2-D1 are further filtered for molecular engineering based on sidechain clashes, locations, charge numbers, solvent accessibility and dynamic properties. Generated preliminary $Ca^{2+}$ binding sites involving residues at conserved positions and residues essential for folding and biological functions were automatically eliminated from further consideration.

Referring back to FIG. 8, the $Ca^{2+}$-binding site of the designed protein (Ca.CD2) was ultimately formed by two discontinuous sections of the polypeptide and includes the oxygens from the side chains of Asp and Asn (D15 and D17 at β-strand B and N60 and D62 at the DE loop). Asp was selected as $Ca^{2+}$ ligand residues because it is known that $Ca^{2+}$ preferentially binds Asp over Glu, especially for the discontinuous $Ca^{2+}$ binding motifs in non-helical proteins and because Asp can serve as either a unidentate or bidentate calcium ligand. Asn was selected because Asn is a common non-charged calcium binding ligand residue. All of the ligand residues are at the surface of the protein with excellent solvent accessibility to accommodate electrostatic interactions between $Ca^{2+}$ and its charged ligand residues and to facilitate water as ligand atoms.

This designed calcium binding site utilizes existing side chain oxygen atoms from N60 and D62 as $Ca^{2+}$ ligands so that mutation and potential structural alteration could be avoided when engineered into CD2. Further, this location does not interfere with the hydrophobic core that is essential for protein folding. Moreover, the location of this site at the BED β-strand layer on the opposite side of the functional cell adhesion surface of CD2 prevents direct interference with the molecular recognition surface for CD48.

Further, it was shown that the introduction of the $Ca^{2+}$-binding site into CD2 does not alter its overall native tertiary structure or its ability to bind its natural ligand (CD48) and conformation-dependent antibodies (O×34 and O×55). Homonuclear and heteronuclear multidimensional NMR spectroscopy confirmed that the solution structure and high-resolution features of the Ca.CD2 protein. The design of calcium binding proteins with desired structural and functional properties demonstrates the potential to understand and manipulate signaling, cell adhesion, and any number of other cellular processes by designing novel calcium-modulated proteins with specifically tailored functions.

The affinities of Ca.CD2 for mono- and divalent cations were examined using the two-dimensional $^{1}H—^{15}N$ HSQC spectra with and without calcium. The majority of the resonances of Ca.CD2 are not perturbed by the addition of $Ca^{2+}$, but several residues, such as D15, D17, I18, N60, D62 and L63, experience significant changes in their chemical shifts. No such changes are observed upon the addition of 130 mM KCl. Moreover, the host protein does not exhibit any significant calcium-induced chemical shift changes. The concurrent change of the NH chemical shifts of these residues as a function of calcium with $K_d$ for $Ca^{2+}$ of 1.4±0.4 mM. The changes in chemical shifts of residues at the designed calcium-binding pocket clearly indicate that calcium binds to the designed calcium-binding site.

The Ca.CD2 protein also was examined using $Tb^{3+}$, which has similar binding properties to $Ca^{2+}$ and is used widely as a probe for $Ca^{2+}$ binding proteins. The close proximity (7.2 Å) of the metal ion to W32 enables the detection of calcium binding by fluorescence resonance energy transfer between the aromatic residue and the bound terbium. As shown in FIG. 10, the addition of Ca.CD2 into a fixed concentration of terbium results in the enhancement of the terbium fluorescent signal at 545 nm, indicating the formation of a $Tb^{3+}$-Ca.CD2 complex. Further, $Tb^{3+}$ fluorescence enhancement gradually increases to saturation at 70 μM $Tb^{3+}$. The addition of $Tb^{3+}$ to CD2 does not lead to a significant change of $Tb^{3+}$ fluorescence enhancement (the same aromatic residues responsible for FRET observed in Ca.CD2 are present in CD2). Thus, by monitoring the change of $Tb^{3+}$ fluorescence enhancement as a function of $Tb^{3+}$ concentration, it was shown $Tb^{3+}$ had a binding affinity of Ca.CD2 or $K_d$=6.6±1.6 μM.

NMR structural microscopy also reveals that $Ca^{2+}$ binds specifically to the designed ligand residues in Ca.CD2 with the designed arrangement. Like natural $Ca^{2+}$ binding proteins, Ca.CD2 also exhibits a good selectivity for $Ca^{2+}$ under physiological conditions of excess $Mg^{2+}$ (3-10 mM) and $K^{+}$ (130 mM). The 1D $^{1}H$ NMR spectra of Ca.CD2 with sequential addition of EGTA (0.050 mM), $K^{+}$ (130 mM), $Mg^{2+}$ (10 mM), and $Ca^{2+}$ (5 mM). As $Ca^{2+}$-induced changes clearly do not result from the presence of high salt, these changes can be assigned to the residues close to the calcium-binding site in the protein. $Ca^{2+}$ and $La^{3+}$ are also able to compete with $Tb^{3+}$ for binding to the designed $Ca^{2+}$ binding site. These results demonstrate that Ca.CD2 is able to bind calcium with good selectivity over excess mono and divalent ions.

In another example of CD2 with a designed calcium binding site, the disassociation constants of the metal binding affinities for $Ca^{2+}$, $Tb^{3+}$, and $La^{3+}$ are 10, 0.10 and 0.3 μM, respectively. Thus, it is possible to vary the disassociation constants.

In another example, a natural magnesium-binding site (Site 2) of calbindin$_{D9k}$ was used for establishing geometric parameters of magnesium binding sites in proteins. The crystal structure of the parvalbumin-magnesium complex (4PAL) then is used to evaluate the structural parameters for magnesium-binding sites. For magnesium-binding sites, a pseudo-residue, aspartate with the attachment of a magnesium atom, was used as the anchor. The magnesium atom is placed 2.1 Å away from the sidechain oxygen atom of aspartate with a Mg—Oδ-Cγ angle of 141° and a Mg—Oδ-Cγ-Cβ dihedral angle of 62.5°. As shown in FIG. 11, an octahedral geometry was used to define the magnesium-binding site. The distance between the magnesium and the ligand oxygen is restricted to 1.0 to 3.0 Å for all four ligands. The ranges for angles of O—Mg—O are set to 30-140° because the ideal value for an octahedral geometry is 90°. The other angles and dihedral angles are not constrained. The remaining parameters for magnesium are identical to those for the EF-hand calcium-binding sites. All of the heteroatoms in these structural files including metal ions and water were deleted from the files.

These examples demonstrate that this invention may be used for designing calcium-selective binding sites in proteins with atomic resolution and biological function. The same design concept can also be used in designing other novel metal-selective and metal-sensitive functional proteins or enzymes and in the construction of new biomaterials, sensors, catalysts, and pharmaceuticals.

10. Terbium Fluorescence

Terbium fluorescence was used to measure fluorescence emitted by any protein or analyte. In a non-fluorescent protein, it was possible to measure the responsiveness of the protein by measuring the fluorescence signal of the analyte, namely, $Tb^{3+}$.

Referring to FIG. 10, Try/Typ-sensitized fluorescent resonance energy transfer experiments were performed on a PTI fluorimeter with slit widths of 8 and 12 nm for excitation and emission respectively. A glass filter with cutoff of 320 nm was used to avoid Raleigh scattering. The emission spectra were collected from 520 to 570 nm with an excitation wavelength at 282 nm. The terbium titration was performed in 100 mM MOPS pH 6.9 by gradually adding terbium stock solution (1 mM) into 2.2 M CD2. Ca1 solution. The same concentration of protein was incorporated into the metal stock solution to avoid dilution of the protein concentration due to titration. Thirty minutes of equilibrium time was allowed between each point. For the metal competition study, the solution containing 30 uM of terbium and 2.2 uM of protein was used as the starting point. The stock solutions of each metal ($La^{3+}$, $Ca^{2+}$, and $Mg^{2+}$) containing the same amounts of terbium and protein were gradually added to the solution. The contribution of $Tb^{3+}$ background to the emission at 545 nm was determined using blank metal solutions with 30 uM $Tb^{3+}$ in the absence of protein for every metal concentration.

The fluorescence intensity at 545 nm was first normalized by subtracting the contribution of the baseline slope. The contribution of intrinsic $Tb^{3+}$ background (blank) was then removed from that of fluorescence intensity of the protein sample. The $Tb^{3+}$-binding affinity of CD2.ca1 was obtained by fitting the $Tb^{3+}$ titration data using the following equation $$f = \frac{([P]_T + [M]_T + K_d) - \sqrt{([P]_T + [M]_T + K_d)^2 - 4[P]_T[M]_T}}{2[P]_T}, \quad (3)$$

wherein f is the factional change, $K_d$ is the dissociation constant, and [P]T and [M]T are the total concentration of protein and metal, respectively.

The metal composition data of CD2.Ca1 was analyzed using the apparent dissociate constant of the competitive metal ion obtained by equation (3). Because CD2.Ca1 is almost saturated with $Tb^{3+}$ at the starting point of competition, this apparent binding affinity has the relationship with the true binding affinities and $Tb^{3+}$ concentration as $$K_{d2} = K_{app} \times \frac{K_{d1}}{K_{d1} + [M_1]}, \quad (4)$$

wherein $k_{d1}$ and $k_{k2}$ are dissociation constants of $Tb^{3+}$ and the competing metal ion, respectively, $K_{app}$ is the apparent dissociation constant, and [M1] is the $Tb^{3+}$ concentration.

11. $Mn^{2+}$ Reasonance

Figure 12:
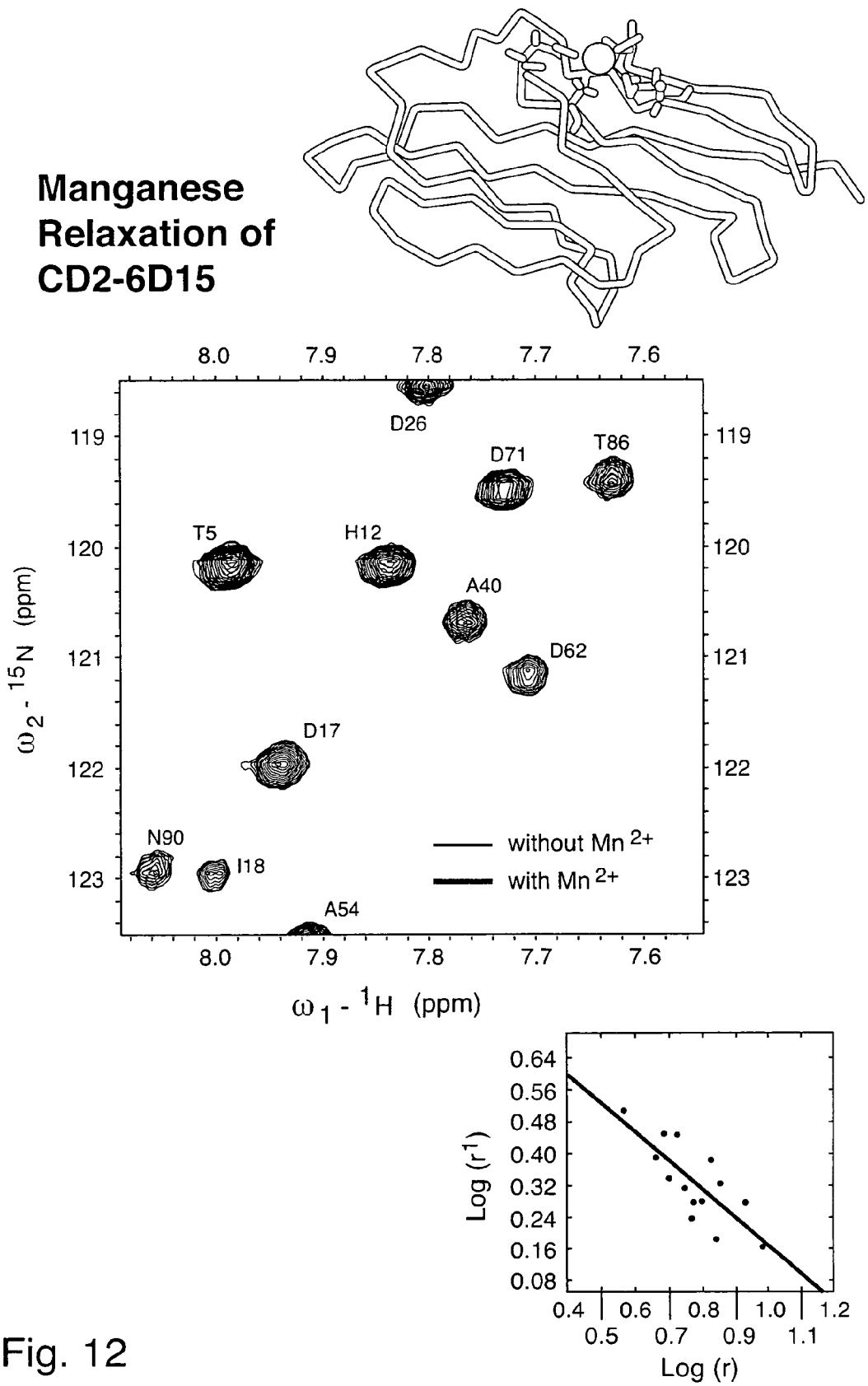
FIG. 12 illustrates an exemplary analysis of an analyte sensor using $Mn^{2+}$ nuclear magnetic resonance.

A CD2 protein (Ca.CD2) was the host protein for a $Mn^{2+}$ binding site as shown in FIG. 12. Paramagnetic ions such as $Mn^{2+}$ (or $Gd^{3+}$) have interactions with proteins that are detectable using nuclear magnetic resonance (NMR). The amino acid residues (A40, A54, D26, D71, H12, N90, T5, and T86) in the metal binding pocket experience a line broadening due to the addition of the paramagnetic ion $Mn^{2+}$. More importantly, the protein in the presence of $Mn^{2+}$ has a quantifiable signal dependant on the $Mn^{2+}$ in the microenvironment. As such, the resonance of paramagnetic ions such as $Mn^{2+}$ has applications on NMR (MRI) technology and can be used as contrast reagents for diagnostics using MRI.

The foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

What is claimed is:

1. An analyte sensor consisting of:
a modified fluorescent protein comprising a single amino acid sequence formed of consecutive amino acids,
where an analyte binding site is formed by inserting an amino acid sequence of the analyte binding site within the single amino acid sequence of the modified fluorescent protein, where the inserted amino acid sequence is formed of consecutive amino acids
where the single amino acid sequence encodes the modified fluorescent protein and the analyte binding site,
where the analyte binding site is incorporated into the internal structure of the modified fluorescent protein and not attached to either a beginning or an end of the modified fluorescent protein,
where the analyte binding site binds to an analyte,
where the modified fluorescent protein includes a single, amino acid-based chormophore including at least two amino acids, and
where the modified fluorescent protein displays fluorescence properties proportional to a concentration of the analyte in a range from 0-20 mM.

2. The sensor as claimed in claim 1, wherein the analyte is a metal ion.

3. The sensor as claimed in claim 2, wherein the analyte is a transition metal ion.

4. The sensor as claimed in claim 2, wherein the analyte is a Group II metal ion.

5. The sensor as claimed in claim 2, wherein the analyte is a Lanthanide series ion.

6. The sensor as claimed in claim 5, wherein the analyte is $Tb^{3+}$.

7. The sensor as claimed in claim 1, wherein the analyte binding site is constructed from a modified natural analyte binding site or a natural analyte motif.

8. The sensor as claimed in claim 7, wherein the analyte binding site comprises at least one EF-hand motif.

9. The sensor as in claim 1, wherein the fluorescent protein is an enhanced Aequora Victoria green fluorescent protein.

10. The sensor as claimed in claim 1, wherein the fluorescent protein is selected from the group consisting of green fluorescent protein, cyan fluorescent protein, yellow fluorescent protein, red fluorescent protein, gold fluorescent protein and combinations thereof.

11. The sensor as claimed in claim 1, further comprising a signal peptide which targets the sensor into a microenviornment.

12. The sensor as claimed in claim 1, wherein a signal peptide targets the sensor into the cytosol of a cell.

13. The sensor as claimed in claim 1, wherein the signal peptide targets the sensor into an endoplasmic reticulum of a cell.

14. The sensor as claimed in claim 8, wherein the fluorescent protein is selected from the group consisting of green fluorescent protein, cyan fluorescent protein, yellow fluorescent protein, red fluorescent protein, gold fluorescent protein and combinations thereof.

15. An analyte sensor consisting of:
a modified fluorescent protein comprising a single amino acid sequence formed of consecutive amino acids,
where an analyte binding site is formed by inserting an amino acid sequence of the analyte binding site within the single amino acid sequence of the fluorescent protein,
where the analyte binding site comprises at least one EF-hand motif including a calcium-binding loop and at least one flanking helix,
where the inserted amino acid sequence is formed of consecutive amino acids and the single amino acid sequence encodes the modified fluorescent protein and the analyte binding site,
where the analyte binding site is incorporated into the internal structure of the modified fluorescent protein and not attached to either a beginning or an end of the amino acid sequence encoding the modified fluorescent protein,
where the analyte binding site binds to an analyte, and
where the modified fluorescent protein includes a single amino acid-based chromophore including at least two amino acids.

16. The sensor as claimed in claim 15, wherein changing charged side chains of the calcium-binding loop varies binding affinity of the analyte binding site.

17. The sensor as claimed in claim 16, wherein changing the charged side chains includes removal of at least one charged side chain.

18. The sensor as claimed in claim 15, wherein modifying the at least one flanking helix varies binding affinity of the analyte binding site.

19. The sensor as claimed in claim 18, wherein the at least one EF-hand motif includes two flanking helices modified with different affinities to the analyte.

20. The sensor as claimed in claim 15, wherein the fluorescent protein is selected from the group consisting of green fluorescent protein, cyan fluorescent protein, yellow fluorescent protein, red fluorescent protein, gold fluorescent protein and combinations thereof.

21. The sensor of claim 15, wherein binding of the analyte to the analyte binding site can cause a change in the fluorescence of the modified fluorescent protein that is not the result of FRET between two distinct molecules.

22. The sensor of claim 1, wherein binding of the analyte to the analyte binding site can cause a change in the fluorescence of the modified fluorescent protein that is not the result of FRET between two distinct molecules.

23. A single amino acid sequence comprising:
amino acids that form a single fluorescent protein;
consecutive amino acids that form an analyte binding site, where the consecutive amino acids that form the analyte binding site are inserted between the C-terminus and the N-terminus of the single fluorescent protein, where the analyte binding site can bind an analyte; and
an amino acid-based chromophore, where the amino acid-based chromophore is formed from at least two of the amino acids that form the single fluorescent protein.

24. The single amino acid sequence of claim 23, wherein binding of the analyte to the analyte binding site can cause a change in the fluorescence of the modified fluorescent protein that is not the result of FRET between two distinct molecules.

25. The single amino acid sequence of claim 24, wherein the analyte binding site is not native to the fluorescent protein.

26. The single amino sequence of claim 24, wherein the analyte binding site is an EF-hand motif.

27. The single amino acid sequence of claim 24, wherein the analyte is a metal ion.

28. The single amino acid sequence of claim 24, wherein the analyte is a transition metal ion.

29. The single amino acid sequence of claim 24, wherein the analyte is a Group II metal ion.

30. The single amino acid sequence of claim 24, wherein the analyte is a Lanthanide series ion.

31. The single amino acid sequence of claim 24, wherein the fluorescent protein is selected from the group consisting of green fluorescent protein, cyan fluorescent protein, yellow fluorescent protein, red fluorescent protein, and gold fluorescent protein.

32. The single amino acid sequence of claim 24, wherein the change in fluorescence is an increase in the amount of fluorescence.

33. The single amino acid sequence of claim 23, wherein the single amino acid sequence consists of:
   amino acids that form a single fluorescent protein;
   consecutive amino acids that form an analyte binding site, where the consecutive amino acids that form the analyte binding site are inserted between the C-terminus and the N-terminus of the single fluorescent protein,
   where the analyte binding site can bind an analyte; and
   an amino acid-based chromophore, where the amino acid-based chromophore is formed from at least two of the amino acids that form the single fluorescent protein.

* * * * *

SEQUENCE LISTING

```
<160> NUMBER OF SEQ ID NOS: 9

<210> SEQ ID NO 1
<211> LENGTH: 308
<212> TYPE: PRT
<213> ORGANISM: Artificial Sequence
<220> FEATURE:
<223> OTHER INFORMATION: Chemically synthesized analyte sensor sequence

<400> SEQUENCE: 1

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Gly Pro Ser Arg Met Val Ser Lys Gly Glu Glu Leu Phe Thr
        35                  40                  45

Gly Val Val Pro Ile Leu Val Glu Leu Asp Gly Asp Leu Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160
```

Arg Ile Glu Leu Lys Gly Ile Asp Phe Lys Glu Asp Gly Asn Ile Leu
            165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
            195                 200                 205

Asn Ile Glu Glu Glu Ile Arg Glu Ala Phe Arg Val Phe Asp Lys
210                 215                 220

Asp Gly Asn Gly Tyr Ile Ser Ala Ala Glu Leu Arg His Val Met Thr
225                 230                 235                 240

Asn Leu Asp Gly Ser Val Gln Leu Ala Asp His Tyr Gln Gln Asn Thr
            245                 250                 255

Pro Ile Gly Asp Gly Pro Val Leu Leu Pro Asp Asn His Tyr Leu Ser
            260                 265                 270

Thr Gln Ser Ala Leu Ser Lys Asp Pro Asn Glu Lys Arg Asp His Ile
            275                 280                 285

Val Leu Leu Glu Phe Val Thr Ala Ala Gly Ile Thr Leu Gly Met Asp
            290                 295                 300

Glu Leu Tyr Lys
305

<210> SEQ ID NO 2
<211> LENGTH: 308
<212> TYPE: PRT
<213> ORGANISM: Artificial Sequence
<220> FEATURE:
<223> OTHER INFORMATION: Chemically synethsized analyte sensor sequence

<400> SEQUENCE: 2

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Gly Pro Ser Arg Met Val Ser Lys Gly Glu Glu Leu Phe Thr
            35                  40                  45

Gly Val Val Pro Ile Leu Val Glu Leu Asp Gly Asp Leu Asn Gly His
            50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
            85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
            115                 120                 125

Glu Gly Tyr Val Gln Glu Arg Thr Ile Phe Phe Lys Asp Asp Gly Asn
130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
            165                 170                 175

Gly His Lys Leu Glu Tyr Asn Tyr Asn Ser His Asn Val Tyr Ile Met
            180                 185                 190

Ala Asp Lys Gln Glu Glu Glu Ile Arg Glu Ala Phe Arg Val Phe Asp
            195                 200                 205

```
Lys Asp Gly Asn Gly Tyr Ile Ser Ala Ala Glu Leu Arg His Val Met
    210                 215                 220

Thr Asn Leu Lys Asn Gly Ile Lys Val Asn Phe Lys Ile Arg His Asn
225                 230                 235                 240

Ile Glu Asp Gly Ser Val Gln Leu Ala Asp His Tyr Gln Gln Asn Thr
                245                 250                 255

Pro Ile Gly Asp Gly Pro Val Leu Leu Pro Asp Asn His Tyr Leu Ser
                260                 265                 270

Thr Gln Ser Ala Leu Ser Lys Asp Pro Asn Glu Lys Arg Asp His Ile
            275                 280                 285

Val Leu Leu Glu Phe Val Thr Ala Ala Gly Ile Thr Leu Gly Met Asp
    290                 295                 300

Glu Leu Tyr Lys
305

<210> SEQ ID NO 3
<211> LENGTH: 99
<212> TYPE: PRT
<213> ORGANISM: Artificial Sequence
<220> FEATURE:
<223> OTHER INFORMATION: Chemically synthesized analyte sensor sequence

<400> SEQUENCE: 3

Arg Asp Ser Gly Thr Val Trp Gly Ala Leu Gly His Gly Ile Asp Leu
1               5                   10                  15

Asp Ile Pro Asn Phe Gln Met Thr Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Ala Phe Glu Ile Leu Ala Asn Gly Asp Leu Lys
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Ile Arg
                85                  90                  95

Ile Leu Glu

<210> SEQ ID NO 4
<211> LENGTH: 99
<212> TYPE: PRT
<213> ORGANISM: Artificial Sequence
<220> FEATURE:
<223> OTHER INFORMATION: Chemically synthesized analyte sensor sequence

<400> SEQUENCE: 4

Arg Asp Ser Gly Thr Val Trp Gly Ala Leu Gly His Gly Ile Asn Leu
1               5                   10                  15

Asn Ile Pro Asn Glu Gln Met Thr Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Ala Phe Glu Ile Leu Ala Asn Gly Asp Leu Lys
    50                  55                  60

Ile Lys Asn Leu Thr Arg Asp Asp Ser Gly Thr Tyr Asn Asn Thr Glu
65                  70                  75                  80

Tyr Ser Thr Asn Gly Thr Arg Ile Asp Asn Ile Ala Leu Asp Ile Arg
                85                  90                  95
```

Ile Leu Glu

<210> SEQ ID NO 5
<211> LENGTH: 5
<212> TYPE: PRT
<213> ORGANISM: Artificial Sequence
<220> FEATURE:
<223> OTHER INFORMATION: Chemically synthesized localization sequence

<400> SEQUENCE: 5

Lys Lys Lys Arg Lys
1               5

<210> SEQ ID NO 6
<211> LENGTH: 26
<212> TYPE: PRT
<213> ORGANISM: Artificial Sequence
<220> FEATURE:
<223> OTHER INFORMATION: Chemically synthesized localization sequences

<400> SEQUENCE: 6

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 7
<211> LENGTH: 4
<212> TYPE: PRT
<213> ORGANISM: Artificial Sequence
<220> FEATURE:
<223> OTHER INFORMATION: Chemically synthesized localization sequence

<400> SEQUENCE: 7

Lys Asp Glu Leu
1

<210> SEQ ID NO 8
<211> LENGTH: 16
<212> TYPE: PRT
<213> ORGANISM: Artificial Sequence
<220> FEATURE:
<223> OTHER INFORMATION: Chemically synthesized localization sequence

<400> SEQUENCE: 8

Met Leu Leu Ser Val Pro Leu Leu Gly Leu Leu Gly Leu Ala Ala Asp
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Chemically synthesized localization sequence

<400> SEQUENCE: 9

Met Leu Leu Ser Val Pro Leu Leu Leu Gly Leu Leu Gly Leu Ala Ala
1               5                   10                  15

Ala Asp